United States Patent
Tejedor Jorge et al.

(10) Patent No.: US 9,757,349 B2
(45) Date of Patent: *Sep. 12, 2017

(54) USE OF CILASTATIN TO REDUCE THE NEPHROTOXICITY OF DIFFERENT COMPOUNDS

(71) Applicant: FUNDACION PARA LA INVESTIGACION BIOMEDICA DEL HOSPITAL GREGORIO MARANON, Madrid (ES)

(72) Inventors: Alberto Tejedor Jorge, Madrid (ES); Alberto Lazaro Fernandez, Madrid (ES); Sonia Camano Paez, Madrid (ES); Ana Maria Torres Redondo, Madrid (ES); Jose Antonio Lazaro Manero, Madrid (ES); Manuela Castilla Barba, Madrid (ES); Maria del Carmen De Lucas Collantes, Madrid (ES)

(73) Assignee: FUNDACION PARA LA INVESTIGACION BIOMEDICA DEL HOSPITAL GREGORIO MARANON, Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 15/233,665

(22) Filed: Aug. 10, 2016

(65) Prior Publication Data
US 2017/0035718 A1 Feb. 9, 2017

Related U.S. Application Data

(63) Continuation of application No. 14/940,669, filed on Nov. 13, 2015, now Pat. No. 9,522,128, which is a continuation of application No. 12/442,249, filed as application No. PCT/ES2008/070137 on Jul. 11, 2008, now Pat. No. 9,216,185.

(51) Int. Cl.
| | |
|---|---|
| *A61K 31/167* | (2006.01) |
| *A61K 31/198* | (2006.01) |
| *A61K 31/282* | (2006.01) |
| *A61K 31/436* | (2006.01) |
| *A61K 31/662* | (2006.01) |
| *A61K 31/7036* | (2006.01) |
| *A61K 31/7048* | (2006.01) |
| *A61K 33/24* | (2006.01) |
| *A61K 45/06* | (2006.01) |
| *A61K 9/00* | (2006.01) |
| *A61K 9/08* | (2006.01) |
| *A61K 31/02* | (2006.01) |
| *A61K 31/047* | (2006.01) |
| *A61K 49/04* | (2006.01) |

(52) U.S. Cl.
CPC .......... *A61K 31/198* (2013.01); *A61K 9/0019* (2013.01); *A61K 9/08* (2013.01); *A61K 31/02* (2013.01); *A61K 31/047* (2013.01); *A61K 31/167* (2013.01); *A61K 31/282* (2013.01); *A61K 31/436* (2013.01); *A61K 31/662* (2013.01); *A61K 31/7036* (2013.01); *A61K 31/7048* (2013.01); *A61K 33/24* (2013.01); *A61K 45/06* (2013.01); *A61K 49/0438* (2013.01)

(58) Field of Classification Search
CPC .. A61K 31/167; A61K 31/198; A61K 31/282; A61K 31/662; A61K 31/7036; A61K 31/7048; A61K 33/24; A61K 45/06; A61K 31/436; A61K 2300/00; A61K 9/0019; A61K 31/047; A61K 31/02; A61K 9/08; A61K 49/0438
See application file for complete search history.

(56) References Cited

U.S. PATENT DOCUMENTS

2007/0082858 A1 4/2007 Steyger et al.

FOREIGN PATENT DOCUMENTS

| WO | 97/37649 A1 | 10/1997 |
|---|---|---|
| WO | 2007/130509 A2 | 11/2007 |

OTHER PUBLICATIONS

"Tienam® I.V. 500 mg monovial," prescribing information of the product Tienam, 1999, retrieved from http://www.msd.es/content/patients/products/prospectos/pp_tienam_500monovial_es.pdf.
Adachi et al., "Primary Structure of Human Microsomal Dipeptidase Deduced from Molecular Cloning," *The Journal of Biological Chemistry* 265(7):3992-3995, Mar. 1990.

(Continued)

*Primary Examiner* — Suzanne Ziska
(74) *Attorney, Agent, or Firm* — Seed IP Law Group LLP

(57) ABSTRACT

Use of cilastatin to reduce the nephrotoxicity of different compounds. The invention refers to use of cilastatin to prepare a medicinal product to reduce the nephrotoxicity of a nephrotoxic compound that enters the cells of the proximal tubule through cholesterol rafts. The invention is based on the discovery that a great number of nephrotoxic compounds, including drugs, enter the cells of the proximal tubule through the cholesterol rafts, and that cilastatin is able to interfere with this transport mechanism, decreasing the nephrotoxicity of such compounds to a variable extent. The nephroprotective effect is common to compounds of different chemical nature and solubility and is specific for the kidney, causing no interference with the effects of nephrotoxic drugs having their targets in other organs. Therefore, administration of cilastatin allows for decreasing the nephrotoxic effects of different drugs without reducing their therapeutic effects.

27 Claims, 20 Drawing Sheets

(56) References Cited

OTHER PUBLICATIONS

Birnbaum et al., "Carbapenems, A New Class of Beta-Lactam Antibiotics," *The American Journal of Medicine* 78(Suppl. 6A):3-21, Jun. 1985.
Breymann et al., "Evaluation of Cisplatin Nephrotoxicity in Coadministration with Imipenem/Cilastatin," *Journal of Cancer Research and Clinical Oncology* 116(Supplement):484, 1990.
Calne et al., "Cyclosporin A in Patients Receiving Renal Allografts from Cadaver Donors," *Journal of the American Society of Nephrology* 9(9): 1751-1756, 1998.
Camano et al., "Cilastatin Attenuates Cisplatin-Induced Proximal Tubular Cell Damage," *The Journal of Pharmacology and Experimental Therapeutics* 334(2):419-429, 2010.
Campbell et al., "β-Lactamase Activity of Purified and Partially Characterized Human Renal Dipeptidase," *The Journal of Biological Chemistry* 259(23):14586-14590, Dec. 1984.
de Lucas Collantes, "Cilastatin Protection from Nephrotoxicity Caused by Cyclosporin A and FK 506," Doctoral Thesis, Universidad Autonoma de Madrid, 2007, p. 108, with English tnraslation.
Gruss et al., "Nephroprotective effect of cilastatin in allogeneic bone marrow transplantation. Results from a retrospective analysis," *Bone Marrow Transplantation* 18:761-765, 1996.
Hammer et al., "Reduction of Cyclosporin (CSA) Nephrotoxicity by Imipenem/Cilastatin After Kidney Transplantation in Rats," *Transplantation Proceedings* 21(1):931, Feb. 1989.
Kao et al., "Renal Failure and Rhabdomyolysis Associated With Sitagliptin and Simvastatin Use," *Diabetic Medicine* 25(10):1229-1230, Oct. 2008.
Köller et al., "Cilastatin (MK 0791) is a Potent and Specific Inhibitor of the Renal Leukotriene $D_4$-Dipeptidase," *Biochemical and Biophysical Research Communications* 131(2):974-979, Sep. 1985.
Kozak et al., "Glutathione-degrading Enzymes of Microvillus Membranes," *The Journal of Biological Chemistry* 257(11):6322-6327, 1982.
Kropp et al., "Metabolism of Thienamycin and Related Carbapenem Antibiotic by the Renal Dipeptidase, Dehydropeptidase-I," *Antimicrobial Agents and Chemotherapy* 22(1):62-70, Jul. 1982.
Kusama et al., "Effect of Cilastatin on Renal Handling of Vancomycin in Rats," *Journal of Pharmaceutical Sciences* 87(9):1173-1176, Sep. 1998.
Link et al., "Interventional antimicrobial therapy in febrile neutropenic patients," *Annals of Hematology* 69:231-243, 1994.
Mang et al., "Influence of imipenem/cilastatin (Zienam) on cisplatin nephrotoxicity," *Archives of Oto-Rhino-Laryngology* 245(6):371-372, 1988.
Markewitz et al., "Reduction of Cyclosporine-Induced Nephrotoxicity by Cilastatin Following Clinical Heart Transplantation," *Transplantation* 57(6):865-870, Mar. 1994.
Morandat et al., "Cholesterol-dependent insertion of glycosylphosphatidylinositol-anchored enzyme," *Biochimica et Biophysica Acta* 1564:473-478, 2002.
Nakamura et al., "Effects of Fosfomycin and Imipenem/Cilastatin on Nephrotoxicity and Renal Excretion of Vancomycin in Rats," *Pharmaceutical Research* 15(5):734-738, 1998.
Nakamura et al., "Effects of Fosfomycin and Imipenem-Cilastatin on the Nephrotoxicity of Vancomycin and Cisplatin in Rats," *Journal of Pharmacy and Pharmacology* 51(2):227-232, Feb. 1999.
Namias et al., "Empiric Therapy of Sepsis in the Surgical Intensive Care Unit with Broad-Spectrum Antibiotics for 72 Hours Does Not Lead to the Emergence of Resistant Bacteria," *Journal of Trauma: Injury Infection & Critical Care* 45(5):887-891, Nov. 1998.
Nitanai et al., "Crystal Structure of Human Renal Dipeptidase Involved in β-Lactam Hydrolysis," *J. Mol. Biol.* 321:177-184, 2002.
Norrby et al., "Enhanced Urinary Recovery of N-Formimidoyl-Thienamycin (MK0787) by Co-Administration of MK0791, An Inhibitor of the Dipeptidase Responsible for Renal Metabolism of MK0787," $21^{st}$ Interscience Conference on Antimicrobial Agents and Chemotherapy, Chicago, IL, Nov. 4-6, 1981, 1 page.
Norrby et al., "Urinary Recovery of N-Formimidoyl Thienamycin (MK0787) as Affected by Coadministration of N-Formimidoyl Thienamycin Dehydropeptidase Inhibitors," *Antimicrobial Agents and Chemotherapy* 23(2):300-307, Feb. 1983.
Norrby, "Imipenem/Cilastatin: Rationale for a Fixed Combination," *Reviews of Infectious Diseases* 7(Supplement 3):S447-S451, Jul.-Aug. 1985.
Nosjean et al., "Mammalian GPI proteins: sorting, membrane residence and functions," *Biochimica et Biophysica Acta* 1331:153-186, 1997.
Perez et al., "Inhibition of brush border dipeptidase with cilastatin reduces toxic accumulation of cyclosporine A in kidney proximal tubule epithelial cells," *Nephrol Dial Transplant* 19:2445-2455, 2004.
Razani et al., Caveolae: From Cell Biology to Animal Physiology, *Pharmacological Reviews* 54(3):431-467, 2002.
Servais et al., "Renal cell apoptosis induced by nephrotoxic drugs: cellular and molecular mechanisms and potential approaches to modulation," *Apoptosis* 13:11-32, 2008.
Seveau et al., "Role of lipid rafts in E-cadherin- and HGF-R/Met-mediated entry of *Listeria monocytogenes* into host cells," *The Journal of Cell Biology* 166(5):743-753, Aug. 2004.
Sido et al., "Nephroprotective Effect of Imipenem/Cilastatin in Reducing Cyclosporine Toxicity," *Transplantation Proceedings* 19(1):1755-1758, Feb. 1987.
Simons et al., "Lipid Rafts and Signal Transduction," *Nature Reviews Molecular Cell Biology* 1:31-41, Oct. 2000.
Smart et al., "Caveolins, Liquid-Ordered Domains, and Signal Transduction," *Molecular and Cellular Biology* 19(11):7289-7304, Nov. 1999.
Sweet, "Organic anion transporter (Slc22a) family members as mediators of toxicity," *Toxicology and Applied Pharmacology* 204(3):198-215, May 2005.
Takeda et al., "Characterization of organic anion transport inhibitors using cells stably expressing human organic anion transporters," *European Journal of Pharmacology* 419(2-3):113-120, May 2001.
Toyoguchi et al., "Nephrotoxicity and drug interaction of vancomycin," *Nihon Yakurigaku Zasshi* 107(5):225-235, May 1996. (English abstract only, 1 page).
Toyoguchi et al., "Nephrotoxicity of Vancomycin and Drug Interaction Study with Cilastatin in Rabbits," *Antimicrobial Agents and Chemotherapy* 41(9):1985-1990, Sep. 1997.
Yamada, "The Fine Structure of the Gall Bladder Epithelium of the Mouse," *J. Biophysic. and Biochem. Cytol.* 1(5):445-458, 1955. (25 pages).
Belitsky et al., "Tissue distribution of cyclosporine A in the mouse: a clue to toxicity?," *Clinical Nephrology* 25(Suppl. 1):S27-S29, 1986.
Campbell et al., "Specificity and inhibition studies of human renal dipeptidase," *Biochimica et Biophysica Acta* 956:110-118, 1988.
Clissold et al., "Imipenem/Cilastatin A Review of its Antibacterial Activity, Pharmacokinetic Properties and Therapeutic Efficacy," *Drugs* 33(3 ):183-241, Mar. 1987.
Humes et al., "Cyclosporine Effects on Isolated Membranes, Proximal Tubule Cells, and Interstitium of the Kidney," *Transplantation Proceedings* 20(3, Suppl. 3):748-758, 1988.
Mihatsch et al., "Morphology of cyclosporine nephrotoxicity in the rat," *Clinical Nephrology* 25(Suppl. 1):S2-S8, 1986.
Ryffel, "Pharmacology of Cyclosporine VI. Cellular Activation: Regulation of Intracellular Events by Cyclosporine," *Pharmacological Reviews* 41(3):407-422, 1989.

USE OF CILASTATIN TO REDUCE THE NEPHROTOXICITY OF DIFFERENT COMPOUNDS

CROSS-REFERENCE TO RELATED APPLICATIONS

This application is a continuation of U.S. application Ser. No. 14/940,669, filed Nov. 13, 2015, now pending, which application is a continuation of U.S. application Ser. No. 12/442,249, filed Mar. 21, 2011, now issued as U.S. Pat. No. 9,216,185, which application is a National Stage Entry of PCT Patent Application PCT/ES2008/070137, filed Jul. 11, 2008, each of which are hereby incorporated by reference in their entirety.

TECHNICAL FIELD

The invention refers to administration of cilastatin to reduce the nephrotoxicity of various compounds. More specifically, the invention refers to use of cilastatin to prepare a medicinal product to reduce the nephrotoxicity caused by any compounds entering the cells of the proximal tubule through cholesterol rafts.

BACKGROUND OF THE INVENTION

Renal dehydropeptidase (DHP-I) (also known as dihydropeptidase 1, microsomal dipeptidase, or EC 3.4.13.19) is a glycoprotein involved in hydrolysis of the peptide bond of dipeptides (Adachi 1990, Campbell 1966) which is mainly located in the brush border of the proximal tubular cells of the kidney. DPH-I is a homodimer with two subunits ($\alpha$, $\beta$), each consisting of a 369-amino acid peptide (42 KDa). The subunits have four potential glycosilation sites, and a highly glycosilated form of 63 KDa may be obtained. The active site of each of the subunits forming the dimer ($\alpha,\beta$) consists of zinc ions which are oriented towards the microvilli of the renal tubule (Nitanai 2002). DHP-I is involved in renal metabolism of gluthatione and in conversion of leukotriene D4 into leukotriene E4 (Kozak 1982) and is to date the only mammalian enzyme able to hydrolyze the beta-lactam ring (Campbell 1984). DHP-I is responsible for hydrolyzing the $\beta$-lactam ring of imipenem, inactivating it (Kaham 1983), but does not affect penicillins or cefalosporins.

DSP-I is anchored to the cell membrane by a covalent bond to a glycosyl-phosphatidyl-inositol (GPI) structure (Adachi 1990). Modification of the cell fate of the protein by the GPI anchor during protein translation is a membrane binding modality of more than 200 proteins in eukaryotic cells. In addition to allowing for protein binding to the membrane, it has important roles, particularly in signal translation or in the recognition process (Nosjean 1997). GPI residues are typically located in membrane domains rich in cholesterol and sphingolipids called cholesterol rafts or CRs (Morandat S 2002).

Different classes of lipid CRs coexist in a same cell. In addition to the classical CRs with no structural proteins, these ordered domains may be enriched in a structural protein component, which dramatically changes the morphology and function of the CR. This emerging protein class is called MORFs (modifiers of raft function). The first MORF identified was caveolin-1 (Cav-1). Three caveolin genes are known; caveolins 1 and 2 are ubiquitously expressed, whereas caveolin-3 is only expressed in astrocytes and muscle cells (Smart 1999).

Cav-1 is integrated into the CR microenvironment, but is also anchored to the cytoskeleton by its cytoplasmic domain. This arrangement allows CRs thus formed to generate dish-like 50-100 nm depressions (caveolae) and may be located or displaced in a regulated manner.

Although caveolae and CRs share certain biochemical properties, location of caveolins in caveolae differentiates those membrane domains. Since their discovery in the 50s (Yamaha 1955), there has been much speculation about the role of caveolins. Caveolae have been implied in multiple functions, including endocytosis, lipid homeostasis, tumorigenesis, calcium transport/regulation, cholesterol transport/regulation, and transcytosis of albumin and other proteins through endothelium (Simons 2000, Razani 2002). In addition, caveolins interact with proteins residing in caveolae. This protein-protein interaction involves, amongst others, the inducible nitric oxide synthetase (NOS 2) (Razani 2002).

The apical transport model based on CRs is based on lipid-lipid and lipid-protein relationships. It has recently been suggested that CRs could be important for transport through an endocytic pathway alternative to that of clathrin-coated vesicles. CRs could serve as an entry point for certain pathogens and toxins, such as *Listeria monocytogenes* (Seveau 2004). However, it had not been suggested that CRs could have any relevance for the transport of drugs known to cause cytotoxicity.

Imipenem is an antibiotic of the carbapenem class launched into the market in 1985. Imipenem is an antibacterial agent of the $\beta$-lactam class with a wide spectrum covering most Gram-negative and Gram-positive aerobic and anaerobic pathogens which has a marked activity against $\beta$-lactamase-producing species.

As other carbapenem antibiotics, imipenem undergoes a species-dependent extensive metabolism, as shown by the low recovery of active drug in urine (Birnbaum 1985, Kaham 1983). In vivo and in vitro studies showed that biotransformation mostly occurred in the kidney through the action of dehydropeptidase I (DHP-I). DHP-I hydrolyzes the $\beta$-lactam ring of imipenem and inactivates it (Kaham 1983). This phenomenon, called post-excretory metabolism, does not affect penicillins or cefalosporins.

The antibacterial spectrum of imipenem was suitable for treating Gram-negative germs, mainly in sepsis of an intestinal or renal origin. Renal degradation of imipenem caused suboptimal levels of active drug in the urinary tract (Kropp H 1982), thus limiting its use for the treatment of systemic infections. This caused preclinical research to be aimed at producing a potential inhibitor of DHP-I. This research program led to development of cilastatin, a compound structurally related to imipenem. The first reported studies in which cilastatin already appeared in combination with imipenem were presented to the 21$^{st}$ Interscience Conference on Antimicrobial Agents and Chemotherapy, held in Chicago in November 1981, by Norrby and colleagues (Norrby 1981).

Cilastatin is a competitive inhibitor of DHP-I that prevents hydrolysis of the peptide bond and opening of lactam rings. In the presence of cilastatin, dihydropeptidase does not open the lactam ring of imipenem, prevents its absorption, and increases urinary excretion of imipenem, reducing its concentration in tubular cells (Clissold 1987, Birnbaum 1985). High doses of imipenem alone may cause tubular toxicity in rabbits, but this effect is prevented by concomitant cilastatin administration (Norrby 1985).

In addition to its well known effect as renal dihydropeptidase inhibitor, cilastatin is able to inhibit organic anion transport systems (OATPs) at basolateral level. This effect has recently been reported, and its implication in metabolism of other drugs has been discussed, with little success because the expected effect of its action upon OATPs would be to increase the circulating levels of the drugs involved and to decrease their overall clearance, exactly the opposite effects to those seen.

The chemical name of cilastatin sodium is the monosodium salt of [R-[R*,S*-(Z)]]-7-[(2-amino-2-carboxyethyl)thio]-2-[[2,2-dimetylcyclopropyl) carbonyl]amino]-2-heptenoic acid. Its empirical formula is $C_{16}H_{25}N_2NaO_5S$, and it has a molecular weight of 380.44 Da. It is an off-white to yellowish white amorphous compound, hygroscopic, and highly soluble in water and methanol (Drusano GL 1984). Its chemical structure is as follows:

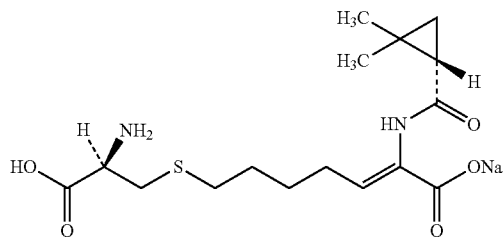

Cilastatin inhibits renal degradation of imipenem, achieving a urinary excretion rate up to 70% of the initial imipenem dose administered. An imipenem:cilastatin (I/C) ratio of 1:1 was established as the optimal dose for maintaining this inhibition for 8 to 10 hours (Norrby 1933). Multiple dose studies showed that cilastatin does not accumulate in healthy subjects.

Cilastatin was demonstrated to have a strong affinity for DHP-I by measuring levels of leukotriene E4, which is formed in the kidney from leukotriene D4 by renal dehydropeptidase in the brush border. In the presence of cilastatin, this conversion was strongly inhibited, which confirmed the cilastatin-DHP-I interaction (Koller 1985, Campbell 1988).

In the 80s, pharmacological research on cyclosporin A and its potential interactions with other commonly used drugs allowed for obtaining evidence that the I/C association could be useful for decreasing imipenem nephrotoxicity. Cyclosporin A (CsA) is a lipophilic cyclic endecapeptide, initially identified as an antifungal, for which a potent immnunosuppressant activity was shown in 1972. It was finally approved for use in 1983. Introduction of CsA, alone or combined with other immunosuppressant agents, has markedly improved immunosuppressive therapy in solid organ and bone marrow transplants, and also in multiple autoimmune diseases. CsA mainly acts upon T cells by inhibiting the cascade of biochemical reactions highly dependent on calcium ion occurring after binding of an antigen to the T-cell receptor and which marks T-cell activation and proliferation through the synthesis of IL-2 (Belitsky 1986, Ryffel 1990).

The main side effect of CsA is nephrotoxicity, which affects both the native kidney (in cases of liver, heart, or bone marrow transplant) and the transplanted kidney (in kidney transplant (Calne 1978). In both cases, the effect is dose-dependent. At tubular level, entry of CsA into the proximal tubule is very rapid. In vitro, 80% of the total is transported in the first 10 minutes at 30° C. (Jackson 1988). Morphological evidence suggests that sublethal tubular damage includes swelling of endoplasmic reticulum, isometric vacuolization, occurrence of autolysosomes, giant mitochondria, microcalcifications, changes in tubular epithelium cytoplasm, necrosis, sloughing of tubular cells, tubular regeneration, and occasional increase in mitosis (Mihatsch 1986). Low CsA doses have been seen to initially cause a significant elevation in intracellular calcium levels before the loss of cell viability. CsA has also been shown to activate proapoptotic genes in tubular and interstitial cells.

However, inclusion of I/C in CsA treatment was seen to decrease renal function impairment in rats (Sido 1987). These experiments were confirmed in nephrectomized rats undergoing kidney transplant (Hammer 1989) and subsequently in humans. It was shown that cilastatin administration may effectively counteract the nephrotoxicity induced by CsA in the period immediately subsequent to a cardiac (Markewitz 1994), bone marrow (Gruss 1996), and kidney transplant (Carmellini 1997, 1998).

As cyclosporin A is not a substrate for DHP-I, the reasons for the nephroprotective effect of concomitantly administered imipenem/cilastatin (I/C) were not known to date, particularly because cilastatin alone was not available, and experiments in which cilastatin or imipenem were separately administered had therefore not been conducted. As a result, such effects could not clearly be attributed to one or the other drug. Mraz (1987, 1992) suggested that the nephroprotective effect, which he attributed to cilastatin, was due to reduction of plasma CsA concentrations. However, Markewitz found no significant differences in CsA doses or in blood levels of CsA or its metabolites, in agreement with Sido (Sido 1987) and Hammer (Hammer 1989). Gruss noted that patients treated with I/C had lower CsA levels than patients not receiving I/C. However, the protective effect of I/C could not be attributed to changes in CsA levels (Gruss 1996).

In 1996, Toyoguchi showed that the I/C combination was able to reduce the nephrotoxicity of vancomycin in rabbits by inhibiting renal vancomycin accumulation (Toyoguchi 1996). One year later, while conducting studies on glomerular filtration of the animal, this author showed that cilastatin alone accelerated renal excretion of vancomycin, decreasing its levels in plasma and renal tissue (Toyoguchi 1997). Although his study included morphological data about vancomycin toxicity on renal tubule, the corresponding study with cilastatin was not provided. These results did not therefore suggest that the combination of both drugs could have clinical value, because an increase in renal excretion of vancomycin would theoretically decrease its effectiveness. Moreover, findings were not specific for the proximal tubule, because I/C decreased vancomycin concentration in both renal cortex and medulla.

Kusama et al conducted a pharmacokinetic study of the influence of the presence of cilastatin in whole animals administered vancomycin (Kusama 1998), and showed that the increase in vancomycin clearance induced by cilastatin was associated to a reduction in vancomycin renal clearance. These authors found no glomerular filtration changes with cilastatin, and could therefore not show any nephroprotective effect, but suggested the existence an potential effect, relating it to inhibition of dehydropeptidase 1 by cilastatin. They also suggested that cilastatin may have an effect on vancomycin reabsorption by the tubule, but as in studies by the Toyoguchi group, they did not conduct any direct study on the subject in cells, and could not therefore show the actual existence of such an effect. Although this group postulated that cilastatin competes with vancomycin for an entry point to the proximal cell, neither its studies nor the subsequent Nakamura studies (Nakamura 1998), in which the decrease in vancomycin excretion in the presence of imipenem/cilastatin was analyzed, allowed for concluding whether this was a competition with reabsorption or with tubular secretion of vancomycin (Nakamura 1998).

Neither CsA nor vancomycin are substrates for renal dipeptidase inhibitable by cilastatin. This is why the suggestions made in discussions of previous studies that a common transport system existed for imipenem and vancomycin met with no great enthusiasm, as it was usually considered that the mechanism by which this effect occurred was not elucidated. Thus, it was not evident for an expert in the technique that cilastatin could serve to decrease the nephrotoxicity of drugs other than those ahead mentioned. Although it has recently been reported that cilastatin is able to inhibit organic anion transport systems (OATP5) at basolateral level, hypotheses about its involvement in metabolism of other drugs have had little success, because the anticipated effect of its action on OATPs would be to increase circulating levels of the involved drugs and to reduce its global clearance. However, the effect usually seen is exactly the opposite. In fact, the brochure provided by the cilastatin manufacturer, Biomol International LP (brochure accessible in the Internet at http://www.biomol.com/SiteData/docs/ProductData/pi153.pdf), describes cilastatin as a dipeptidase inhibitor that inhibits hydrolysis of β-lactam antibiotics, attributing its nephroprotective action against the side elects of cyclosporin A to inhibition of dipeptidase of the brush border of the proximal tubule.

Cyclosporin is apolar, very sparingly soluble in water and soluble in lipids and organic solutes, and the chance that it reaches the inside of cells of the proximal tubular epithelium using the organic anion transport system (OATP) is very low. Until now, its transport mechanism was considered to be transmembrane passive diffusion. Vancomycin has an amphoteric nature and is water-soluble, and could be a theoretical substrate for OATPs of the proximal tubule, but nobody has directly studied such possibility.

All in all, it was not obvious either for experts in the technique that there was any compound which could have an effect on the nephrotoxicity of multiple drugs, or even on nephrotoxic compounds with no known therapeutic activity, decreasing their harmful effects on the renal proximal tubule. This would however be of great interest, because nephrotoxicity is a problem that affects many drugs and limits administration of doses which would be required to achieve their effect on the condition intended to be treated. Nephrotoxic effects require dose reduction or drug discontinuation before full treatment has been administered. Therefore, identification of any compound that decreases the nephrotoxicity of a high number of drugs with nephrotoxic potential would be of great interest for clinical practice. The possibility of inhibiting a common entry mechanism would be a way to achieve this. This invention provides a solution to that problem.

DESCRIPTION OF THE INVENTION

The invention provides for use of cilastatin to manufacture a medicinal product to reduce nephrotoxicity of compounds entering the cells of the renal proximal tubular epithelium through cholesterol rafts.

It is based on the discovery, disclosed in this descriptive report, that a great number of drugs and other compounds with a known nephrotoxic effect, whose transport mechanism to the inside of cells of the proximal tubular epithelium was unknown or was described to other membrane molecules, enter the cells through a pathway that is dependent on cholesterol rafts. This transport pathway appears to be a general mechanism independent from the chemical nature of the transported compound, because the tested compounds for which such transport has been detected (most of them drugs with a recognized therapeutic value but for which nephrotoxicity is a major disadvantage) include both polar and apolar, cationic or neutral compounds, both lipid and water soluble. The solubility and acidity/basicity of such compounds are shown in the table below:

TABLE 1

Chemical characteristics of the nephrotoxic compounds with which the nephroprotective effect of cilastatin has been tested:

| DRUG | ACIDITY/ BASICITY | SOLUBILITY IN ORGANIC MEDIA | SOLUBILITY IN WATER |
|---|---|---|---|
| CYCLOSPORIN | apolar | high | low |
| TACROLIMUS | apolar | high | insoluble |
| VANCOMYCIN | amphoteric | — | high |
| GENTAMICIN | neutral | soluble in DMF insoluble in organic solutes | soluble in water |
| CISPLATIN | neutral | DMF (9.7 mg/kg) | 0.253 g/100 g |
| ACETAMINOPHEN | neutral | soluble in ethanol and acetone insoluble in serum | moderately soluble in hot water |
| FOSCARNET | anionic | insoluble | soluble in water |
| IOPAMIDOL | anionic | soluble in methanol insoluble in chloroform | soluble in water |
| CHLOROFORM | apolar | soluble | miscible in water |
| AMPHOTERICIN | anionic | soluble in DMF (2-4 mg/mL), DMF + HCl (60-80 mg/mL) DMSO (30-40 mg-mL) | soluble in water at pH 2 or pH 11 (0.1 mg/mL) |
| MANNITOL | anionic | soluble in glycerol insoluble in ether | soluble in water (1 g/5.5 mL) |

Tests shown in the Examples of this report demonstrate that cilastatin is able to interfere with this transport mechanism by decreasing accumulation of the main nephrotoxics in renal tubular cell, thereby reducing the damage caused by them to the proximal tubule. Cilastatin also results in reduction of both early and late events associated to death from apoptosis of proximal tubular cells and in restoration of the morphology and regenerative capacity of the tubular epithelium when administered concomitantly with the nephrotoxic whose effect is intended to palliate.

Administration of cilastatin is therefore able to decrease the nephrotoxicity of a compound that enters the cells of the renal proximal tubular epithelium using a transport mechanism in which DHPI containing cholesterol rafts are involved. This leads to the use proposed in the invention.

In addition, the specificity conferred to cilastatin action by its targeting of a protein that is only located in the cholesterol rafts of the proximal tubule allows for assuming (as suggested by tests reported in Example 6 below) that it will have no effect upon cells with no brush border (DPH-I-free) and will thus exert a kidney-specific effect. This makes cilastatin particularly adequate for use in various clinical conditions, combined with drugs targeted to different tissues, with no reduction occurring in the pharmacological activity of the drugs in their target organs.

Thus, in a realization of invention, the compound whose nephrotoxicity is intended to be reduced is a drug. A drug other than cyclosporin A, vancomycin, or imipenem is preferred. In a realization preferred to the above, the drug is selected among gentamicin, tacrolimus, cisplatin, foscarnet, mannitol, iopamidol, amphotericin, and acetaminophen.

Whatever the drug, a preferred realization of the invention is one in which the manufactured medicinal product contains both cilastatin and the drug whose nephrotoxic effects are intended to be reduced because this facilitates their concomitant administration, but they may be part of the same pharmaceutical dosage form (suspension, solution, tablet, freeze-dried powder . . . ) or of different pharmaceutical dosage forms but be included in a same medicinal product (e.g. contained in two different vials or ampoules). This latter dosage form allows for administering cilastatin at different relative ratios to the nephrotoxic drug, or even for deciding whether both compounds are given to the subject to be treated simultaneously or separated by a time interval. Simultaneous administration of both drugs to the subject is particularly preferred. However, cilastatin may be administered as divided doses separated by an interval. The first such dose is preferably administered at the same time as the drug whose nephrotoxic effect wants to be reduced, and other cilastatin doses may be administered in the period between successive dose of the nephrotoxic drug. Cilastatin may be administered by the oral or parenteral (intramuscular, intraperitoneal, or intravenous) routes. Administration of cilastatin by the parenteral route, especially by the intravenous route (which is the most common form of parenteral administration in humans) is preferred. The medicinal product including cilastatin should therefore preferably be designed to be administered by parenteral route, e.g. a solution in saline or other adequate, pharmaceutical acceptable solvent. Preferred dosage forms also include those allowing for easy preparation of cilastatin solutions or suspensions at the desired concentration at the time of administration, such as powder presentations.

As discussed above, drugs tested have different pharmacological effects (antibiotic, cytotoxic, anti-inflammatory, antiretroviral, anesthetic, and immunosuppressant drugs). Specifically, the following compounds have been tested in the Examples provided below in this report:

TABLE 2

Formula and activity of the nephrotoxic compounds with which the nephroprotective effect of cilastatin has been tested:

| Compound | Chemical formula | Description |
| --- | --- | --- |
| Cyclosporin A (CsA) | | Cyclic endecapeptide with chemical formula $C_{62}H_{111}N_{11}O_{12}$ and a molecular weight of 1202.16 Da. It is used as immunosuppressant. |

TABLE 2-continued

Formula and activity of the nephrotoxic compounds with which the nephroprotective effect of cilastatin has been tested:

| Compound | Chemical formula | Description |
|---|---|---|
| Gentamicin | | Aminoglycoside antibiotic with chemical formula $C_{12}H_{43}N_5O_7$ and a molecular weight of 449.5. |
| Tacrolimus | | Macrolide whose empirical formula, in its monohydrate form, is $C_{44}H_{69}NO_{12}$, and with a molecular weight of 822 Da. It is used as immunosuppressant |
| Vancomycin | | Glycopeptide antibiotic with a complex structure. Its empirical formula is $C_{16}H_{25}Cl_2N_9O_{24}$ and its molecular weight 1485.7 Da. |

TABLE 2-continued

Formula and activity of the nephrotoxic compounds with which the
nephroprotective effect of cilastatin has been tested:

| Compound | Chemical formula | Description |
|---|---|---|
| Cisplatin | $Pt(NH_3)_2Cl_2$ (structure) | Chemotherapeutic agent containing platinum (diaminodichloroplatinum (trans)). Empirical formula: $Pt(NH_3)_2Cl_2$, and molecular weight of 300 Da. |
| Iodinated contrast (Iopamidol) | (structure) | Used for diagnosis by a nephrotoxic radiological contrast. Empirical formula $C_{17}H_{22}I_3N_3O_8$ and molecular weight of 777.09 D. |
| Foscarnet | $3\,Na^+\,[\,^-O-P(=O)(O^-)-C(=O)-O^-\,] \cdot 6\,H_2O$ | Antiretroviral. Pyrophosphate analog. |
| Mannitol | (structure) | Alcoholic sugar analog with formula $C_6H_{14}O_6$ and molecular weight of 182.17 Da. It is used as an osmotic diuretic. |
| Amphotericin B | (structure) | Macrolide antifungal with an empirical formula $C_{47}H_{73}NO_{17}$ and a molecular weight of 924.07902 Da. |
| Chloroform | $CHCl_3$ | Toxic compound that may enter the body by inhalation, intake, or throught the skin. Chloroform inhalation or intake for long periods may damage the liver, kidneys, skin, and central nervous system. Sporadic exposure to very high levels may cause death. |
| Acetaminophen | (structure) | Antipyretic analgesic derived from acetanilide, with empirical formula $C_8H_9NO_2$ and molecular weight of 151.16256 Da. |

As may be seen based on their formulas and the characteristics given in Table 1, they all are compounds of a different nature. For drugs for which a second mechanism of cellular penetration may exist because of their anionic nature or because they are extremely lipophilic, the nephroprotective effect of cilastatin could be lower if such mechanism is not inhibited by the latter. In addition to the transport system described here in which cholesterol rafts are involved, drugs of an anionic nature at physiological pH may also enter the renal cell through the organic anion transport system (OATPs). The nephroprotective effect of cilastatin administration is therefore lower in drugs of an anionic nature, such as amphotericin B, because they have an alternative mechanism for cell entry that is not inhibited by cilastatin. This is why one of the preferred realizations of the invention is one in which the drug is of a cationic or neutral nature at physiological pH, at the normal blood pH of 7 or close to 7. As may be seen in Table 1, of compounds with which the tests discussed in the Examples, related to the nephroprotective effect of cilastatin, have been conducted gentamicin, cisplatin, and acetaminophen show a neutral at physiological pH, while foscarnet, iopamidol, amphotericin, and mannitol are anionic at such pH. Cyclosporin, tacrolimus, and chloroform are of an apolar nature, and could therefore also enter the proximal tubular cells by passive diffusion.

At any rate, and as previously mentioned, preferred realizations of the invention include those where the drug is:
  gentamicin;
  tacrolimus;
  foscarnet;
  acetaminophen;
  cisplatin;
  amphotericin;
  mannitol; or
  iopamidol.

In a particularly preferred realization of the invention, the nephrotoxic drug is foscarnet (phosphonoformic acid, normally administered as its trisodium salt hexahydrate), a pyrophosphate analog that specifically inhibits the DNA polymerase of herpesviruses and also has anti-HIV activity. Foscarnet is used for the treatment of retinitis caused by cytomegalovirus in AIDS patients treated with AZT, and also for infections caused by herpesviruses resistant to AZT. Its main adverse effect is precisely its renal toxicity, which limits its use.

In another particularly preferred realization of the invention, the nephrotoxic drug is acetaminophen (N-(4-hydroxyphenyl)ethanamide), also known as paracetamol, a drug with a known analgesic and antipyretic activity whose widespread use, often without awareness that the normal dose is close to overdose, has led to frequent intoxications, and even to use in suicidal attempts. Although the most common effect of an acetaminophen overdose (a single acetaminophen dose of 10 g or continued doses of 5 g/day in a healthy subject not drinking alcohol or 4 g/day in a usual alcohol drinker could lead to toxicity) is liver damage. Renal failure is also common and would have to be palliated in the event of an excess intake of this drug.

In another particularly preferred realization of the invention, the nephrotoxic drug is cisplatin (cis-diaminodychloroplatin II). Cisplatin is a simple platinum compound used as an antineoplastic agent against a variety of tumors (ovary, testis, bladder, head and neck, lung, endometrium. However, cisplatin has potentially lethal adverse effects affecting different organs, the most common of which is nephrotoxicity, which limits its use. Cisplatin treatments must often be stopped, or its doses should be reduced to levels much lower than those desirable to achieve the chemotherapeutic effect sought, due to nephrotoxicity caused by the drug. This is why the search for methods to attempt and reduce its nephrotoxic effect without decreasing its chemotherapeutic activity has become a significant problem for which co-administration with cilastatin represents a promising solution. As generally discussed for any other drug, administration of cilastatin may be previous, concomitant, or subsequent to cisplatin administration, may consist of more than one dose, and the administration route may the same as or different from the administration route of cisplatin. Cilastatin should preferably be administered by the parenteral route (an intravenous route is preferred in humans, although in rat experiments the parenteral administration form used is often the intraperitoneal route), and the preferred cilastatin dosage is at least 750 mg/day as a daily dose or as two divided daily doses.

In another realization of the invention, the compound has no known activity as a drug, but is any other nephrotoxic agent whose effects want to be limited which may have been administered to a subject for different reasons, either accidental or not. Thus, the medicinal product in whose manufacture cilastatin is used could also serve to mitigate the harmful effects on the kidney of different compounds of a toxic nature acting upon it, such as voluntarily or accidentally ingested or inhaled poisons, administering such medicinal product after entry of the nephrotoxic compound into the organism to be treated, or even at the same time of such entry. In this latter situation, cilastatin could serve as an antidote for the nephrotoxic effects of any compound when such compound was voluntarily taken.

Another aspect of the invention is a therapeutic method to reduce the nephrotoxicity of a compound consisting of administration of cilastatin to a subject in whom reduction of the nephrotoxic effect is desired. The compound whose nephrotoxicity is intended to be reduced should preferably be a drug. Cilastatin may be administered at the same time as the drug whose nephrotoxic effect is intended to be reduced, but also before and/or after administration of the nephrotoxic drug. Such administration may occur as a single or divided doses, the first of which may be prior, concomitant, or subsequent to administration of the nephrotoxic drug. A drug other than cyclosporin A, vancomycin, or imipenem is preferred. More preferably, the drug is selected among gentamicin, tacrolimus, cisplatin, foscarnet, mannitol, amphotericin B, and acetaminophen.

In the therapeutic method of the invention, cilastatin may be administered by the oral, intramuscular, intraperitoneal, or intravenous route (of which the last three may be considered as parenteral routes, i.e. routes by which drug entry into the bowel and drug passage to blood by mechanisms associated to the bowel are avoided). Cilastatin should preferably be administered by a parenteral route, especially the intravenous route, e.g. as a solution in saline or other adequate, pharmaceutically acceptable solvent. For parenteral administration, cilastatin dosage should preferably be at least 750 mg/day, which may be administered as a single daily dose or at least two divided daily doses.

An additional aspect of the invention is a composition comprising a nephrotoxic drug and cilastatin. A preferred realization of the invention is one in which the composition does not include imipenem. It is particularly preferred that the nephrotoxic drug is other than cyclosporin A or vancomycin, and very particularly that the nephrotoxic drug is selected among gentamicin, tacrolimus, cisplatin, foscarnet, mannitol, amphotericin B, and acetaminophen. In any of the cases, the composition may include at least one pharmaceutically acceptable vehicle and may be provided as a powder or solution, among other forms. In the latter case, the preferred solvent is saline. In any of the realizations, the composition should preferably be designed to reduce nephrotoxicity of the nephrotoxic drug in the subject to whom it is administered.

The invention will now be explained in greater detail using the following Figures and Examples.

SHORT DESCRIPTION OF FIGURES

FIGS. 1A and 1B refer to blockade of circulation of cholesterol rafts by cilastatin. The figures show the fluorescence due to fluorescent toxin B in cells of pig proximal tubular epithelium in a primary culture, specifically:

FIG. 1A shows the change in fluorescence over time in control cells (upper photographs of the right side of the figure) and cells incubated in the presence of cilastatin (Control+RRbp-x)

FIG. 1B is a graph representing the fluorescence seen in the Golgi apparatus 2.5 hours after caveolae in membranes were labeled with fluorescent B toxin (B-FITC toxin), expressed as the number of cells per square millimeter showing such fluorescence (no. of cells/mm$^2$), in control cells (blank bar) and cells treated with cilastatin (bar with continuous dark filling) or filipin (bar filled with vertical lines).

FIG. 2 shows the lack of harmful effects of cilastatin on cells and cell growth during the days of culture, expressed as thousands of cells seen per square centimeter (cells×1000/cm$^2$), in a primary culture of cells of pig proximal tubular epithelium in the absence of cilastatin (control) or in the presence of the cilastatin (CIL) concentrations given in the figure.

FIG. 3 refers to reduction or absence of cell apoptosis in the presence of cilastatin. The graph shows the oligonucleosome enrichment factor, calculated as compared to control cells incubated without nephrotoxics (first pair of bars), observed when primary cultures of pig proximal tubular cells were incubated with the indicated nephrotoxics in the absence (first bar of each pair, blank) or the presence of cilastatin (second bar of each pair, filled in black) *: ANOVA: effect of cilastatin on each drug: $p<0.05$.

FIG. 4A shows the flow cytometries of supernatants from primary cultures of proximal tubular cells incubated with cisplatin (graphs of left column) or vancomycin (graphs of right column) in the absence or presence of cilastatin (RRbp-X) (lower graphs in both cases).

Figure 4A:
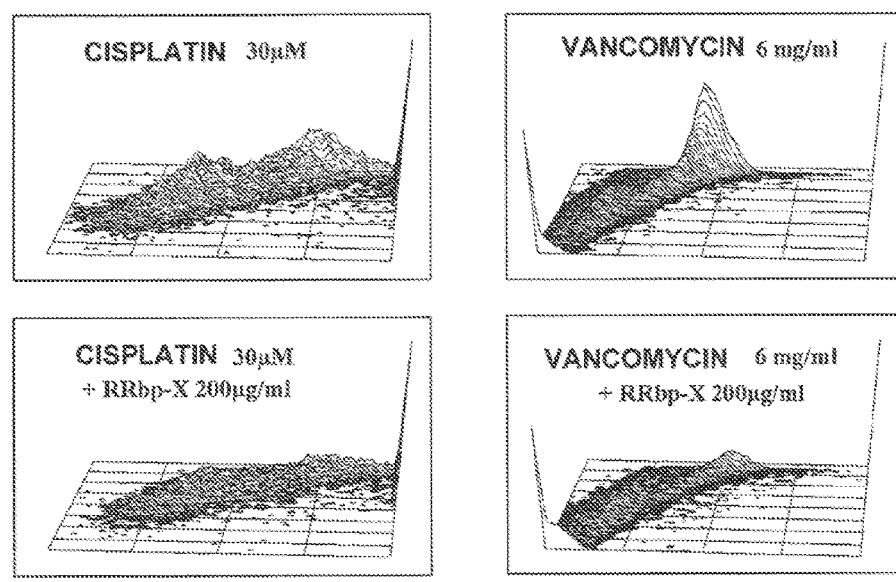
FIGS. 4A-4C show that cilastatin prevents or reduces cell death by anoikis.
Figure 4B:
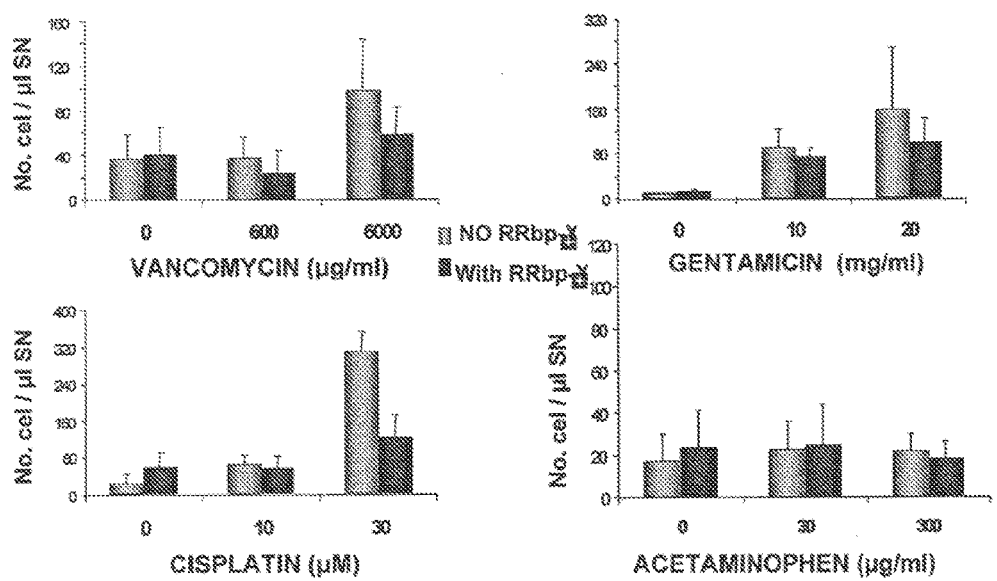

FIG. 4B shows the count of sloughed cells detected per microliter of supernatant (No. cel/μl SN) when primary cultures of proximal tubular cells were incubated with the doses indicated in the X-axis of the nephrotoxic drugs vancomycin, gentamicin, cisplatin, and acetaminophen, as indicated below each graph. From each pair of bars, the initial bar (bars with light grey filling) corresponds to the value obtained at incubation with the nephrotoxic, and the second bar (bars with dark grey filling) to the value obtained after co-incubation with cilastatin (RRbp-X).

Figure 4C:
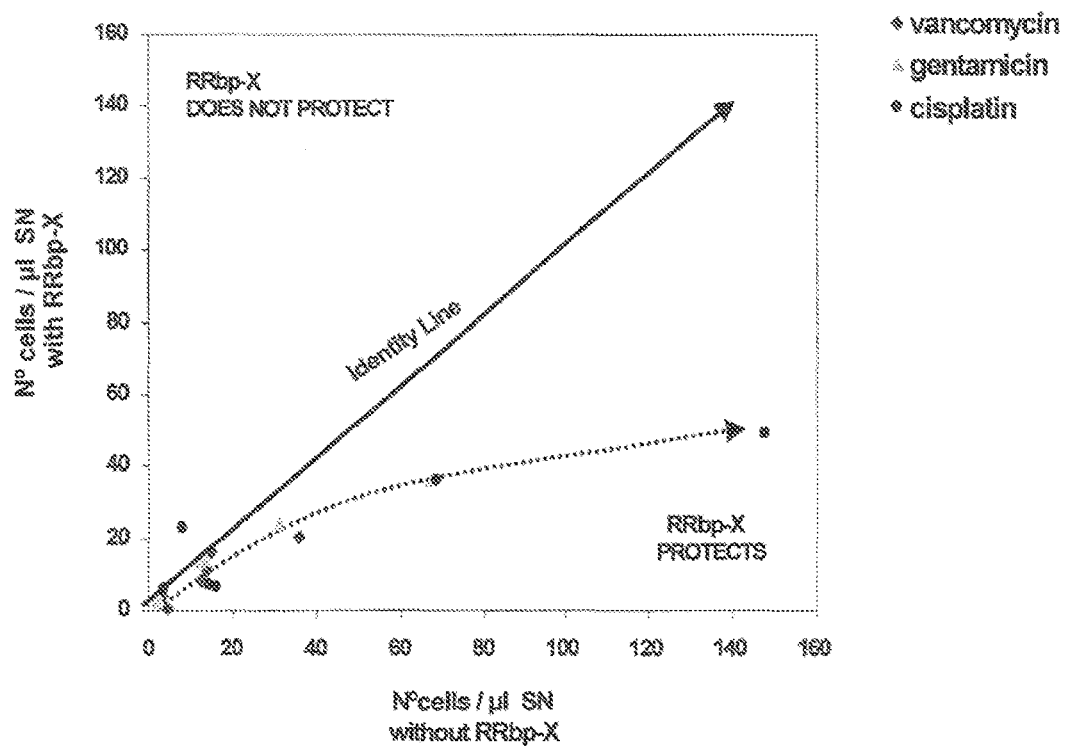

FIG. 4C shows the counts of cells shed to the supernatant after incubating cultures of proximal tubular cells with the nephrotoxic drugs vancomycin (data indicated by diamonds, ♦), gentamicin (data indicated by triangles, ▲), or cisplatin (data indicated circles, ●). Values obtained in incubations without cilastatin are given in the X-axis, while values after incubations with ciiastatin (RRbp-X) appear in the Y-axis. The identity line that would be obtained if the values found in the presence or absence of cilastatin were identical for each nephrotoxic is also represented.

Figure 5A:
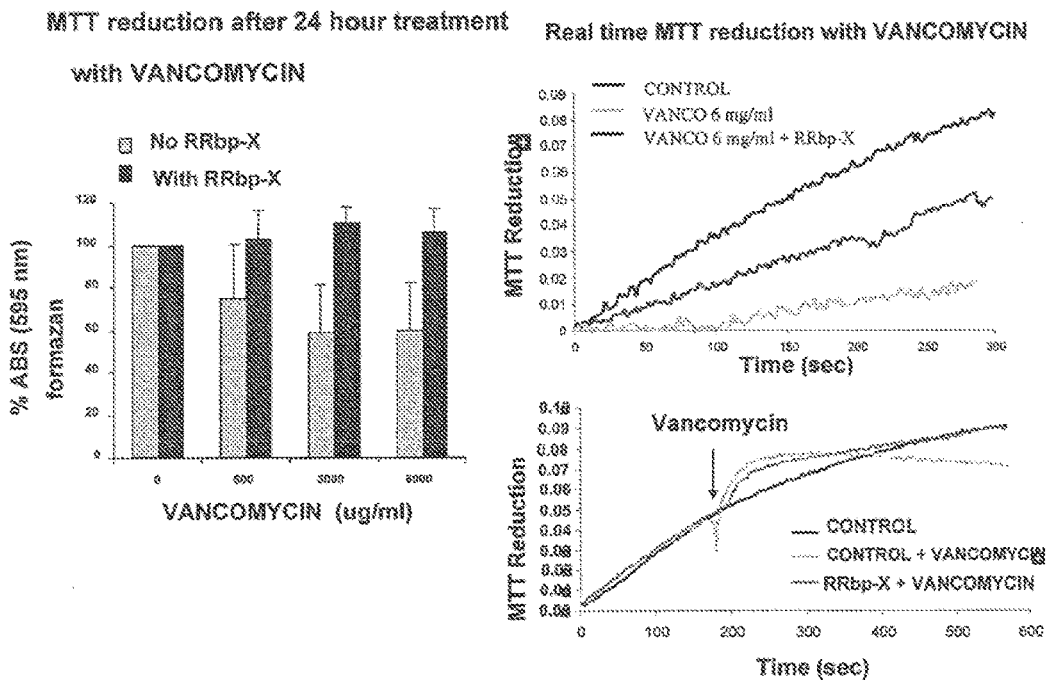
Figure 5B:
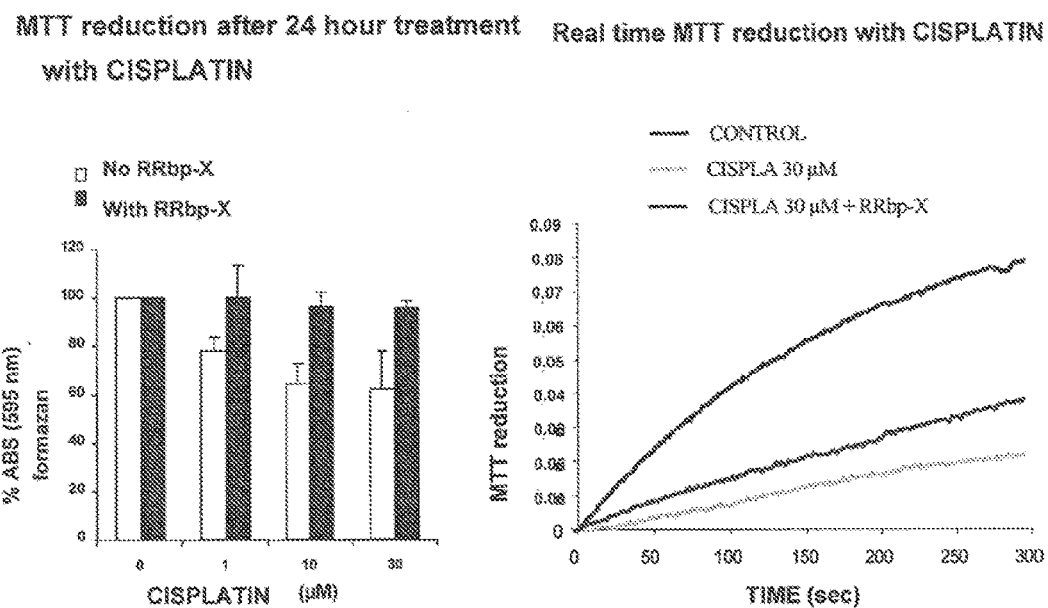
Figure 5C:
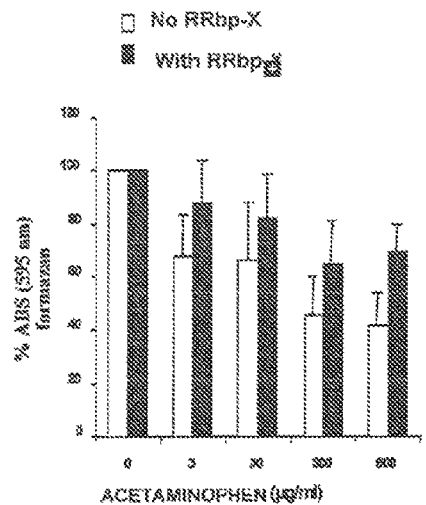
Figure 5C:
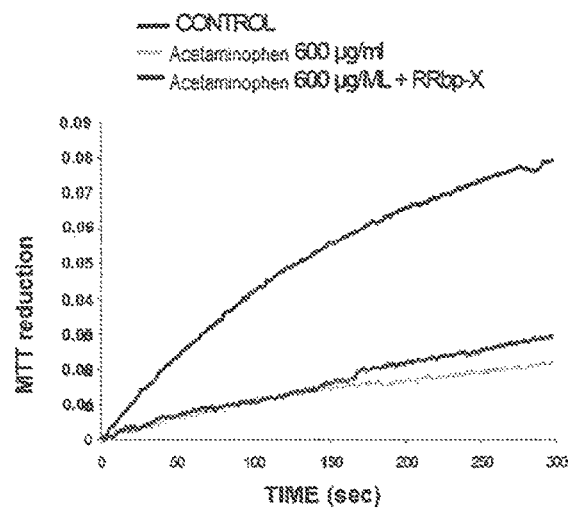
Figure 5D:
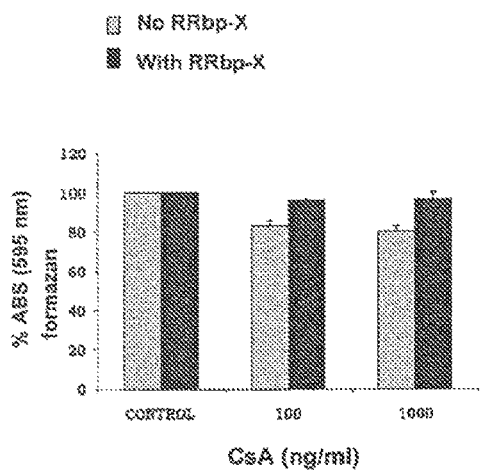
Figure 5D:
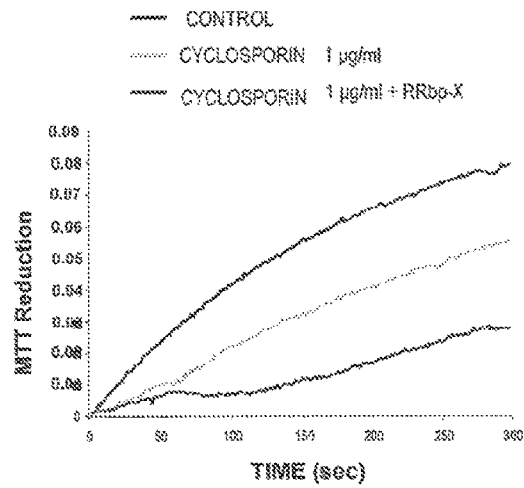
Figure 5E:
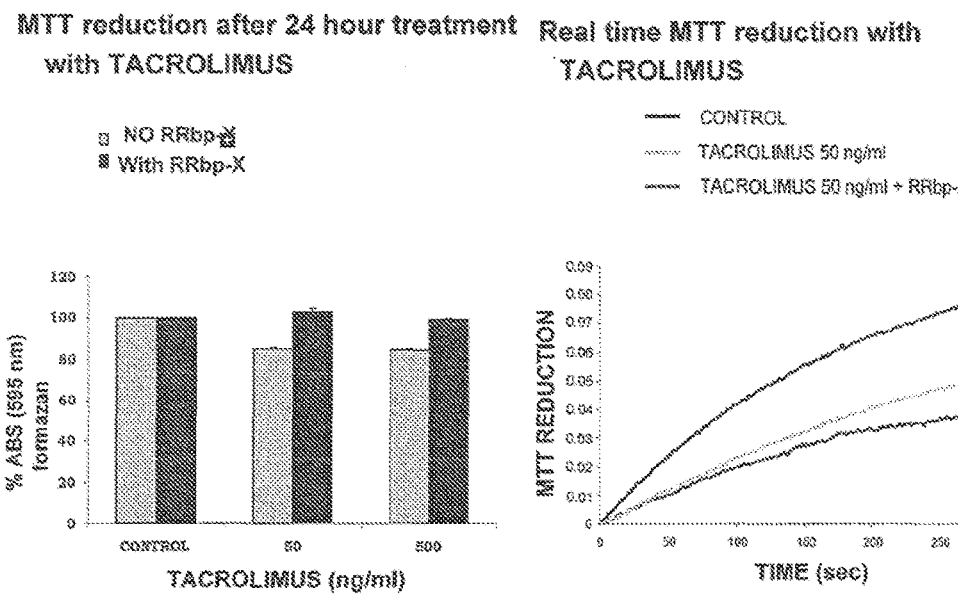

FIGS. 5A-5E refer to restoration of the mitochondrial oxidative capacity of the proximal tubule in the presence of cilastatin. MTT reduction (leading to the occurrence of a blue compound, formazan) by tubular proximal cells in primary culture incubated with the nephrotoxics indicated in each graph is shown. Graphs on the left correspond to occurrence of formazan (measured as relative increase in medium absorbance at 595 nm) as seen in cells incubated for 24 hours with the nephrotoxic concentrations given in the X-axis in the absence (first bar of each pair, with a lighter filling or blank) or presence of cilastatin (second bar of each pair, filled in black). Graphs on the right correspond to formation of formazan as detected in isolated cells in real time with no treatment (control) or incubated with the nephrotoxic concentrations stated in the graph in the absence or presence of cilastatin (RRbp-X) after the incubation times in seconds given in the X-axis. The nephrotoxic drugs for which results are given include vancomycin (FIG. 5A), cisplatin (FIG. 5B), acetaminophen (FIG. 5C), cyclosporin (FIG. 5D), and tacrolimus (FIG. 5E).

Figure 6:
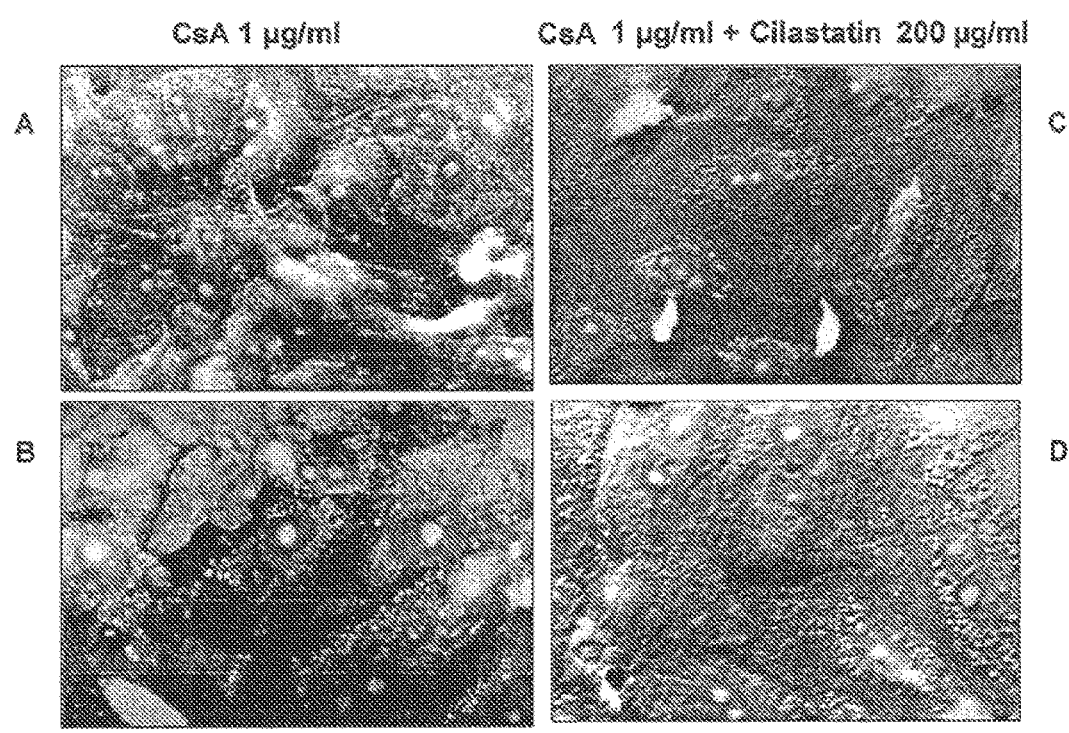

FIG. 6 demonstrates that cilastatin restores cell morphology. The figure shows photographs obtained by scanning electron microscopy of cultures of proximal tubular cells incubated in the presence of 1 μg/mL of cyclosporin (CsA 1 μg/mL, photographs A and B) or in the presence of 1 μg/mL of cyclosporin and 200 μg/mL of cilastatin (photographs C and D).

Figure 7A:
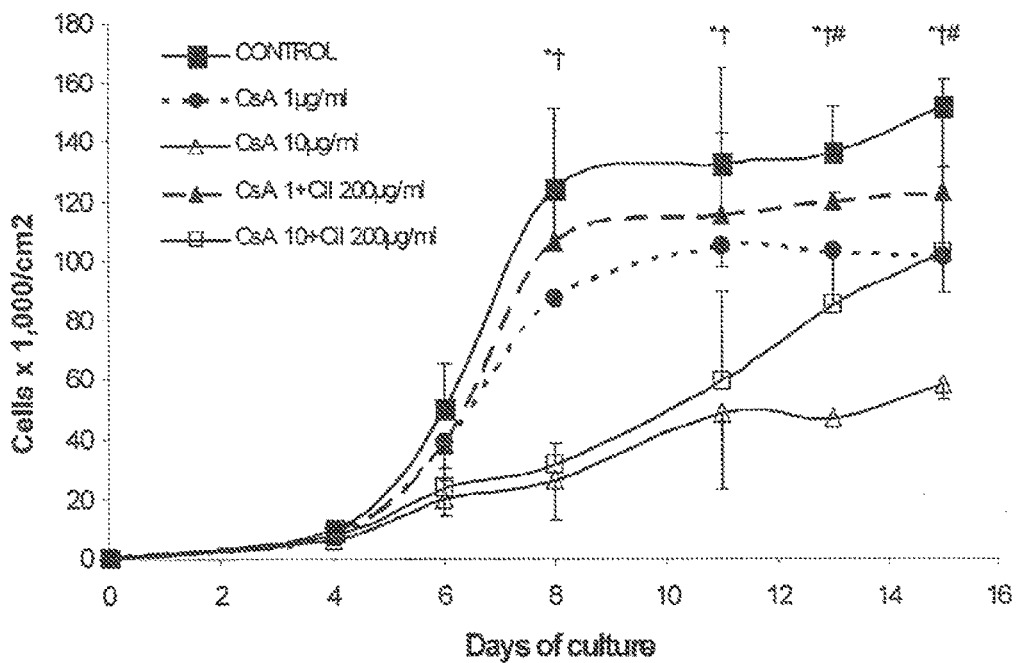
Figure 7B:
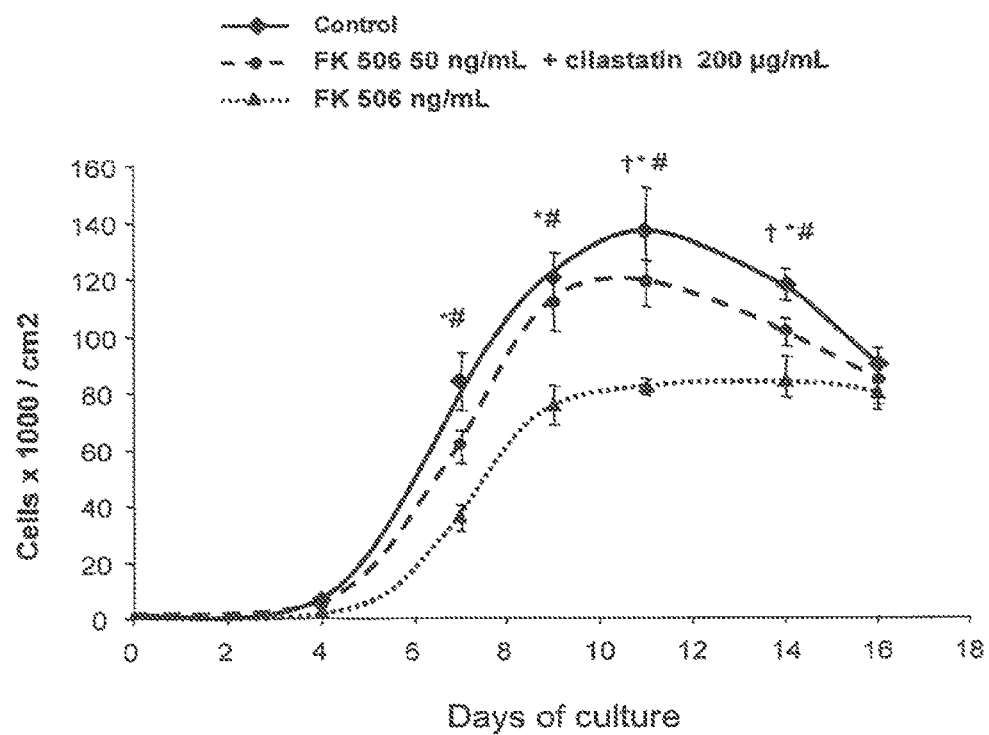

FIGS. 7A and 7B refer to the improved cell recovery following aggression seen in the presence of cilastatin. The figures show growth over the days of culture, given as thousands of cells seen per square centimeter (cells×1000/cm$^2$), of the primary culture of proximal tubular cells in the absence (control) or presence of the amounts stated in the graphs of the nephrotoxic drugs cyclosporin (CsA) (FIG. 7A) or tacrolimus (FK 506) (FIG. 7B), in the absence or presence of cilastatin (Cil). In FIG. 7A, the symbols on the graphs have the following meanings. *: cyclosporin vs. control, $p<0.05$; †: cilastatin+cyclosporin vs. control, $p<0.05$; #: cilastatin+cyclosporin vs. cyclosporin, $p<0.05$. In FIG. 7B, the meanings are similar: *: FK506 vs. control, $p<0.05$; †: FK506+cilastatin vs. control, $p<0.05$; #: FK 506+cilastatin vs. FK 506, $p<0.05$.

Figure 8A:
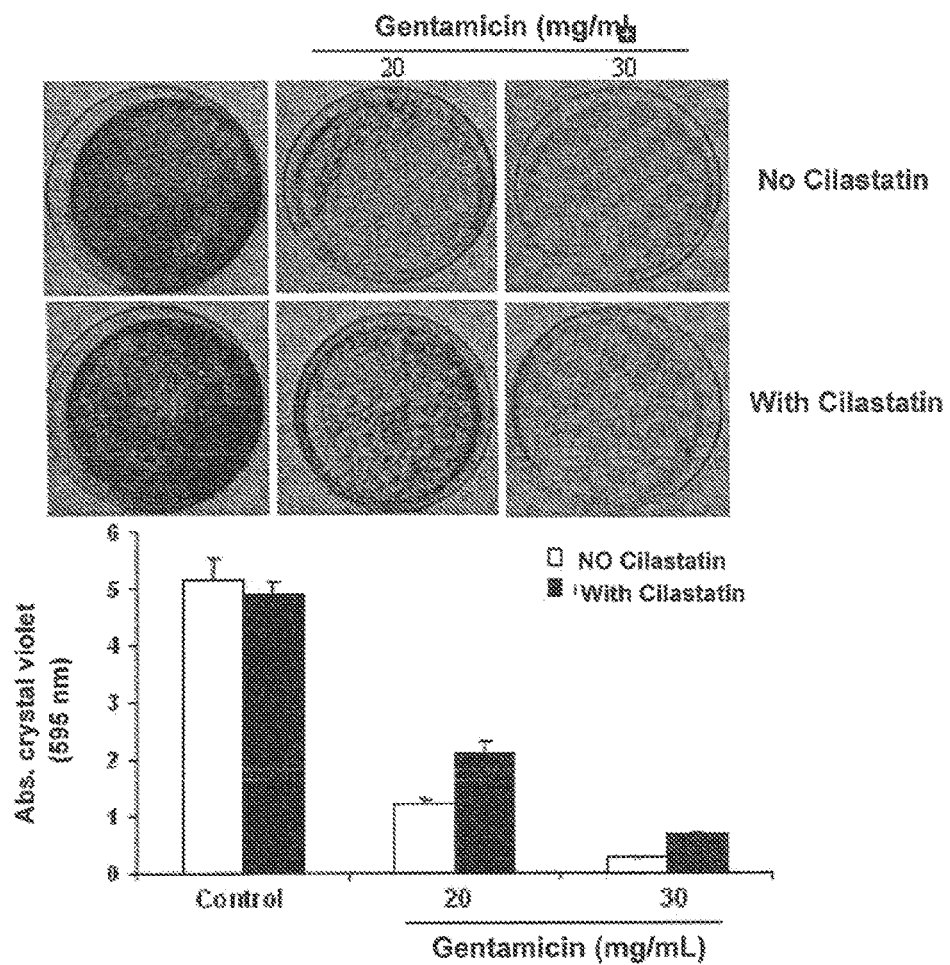
Figure 8B:
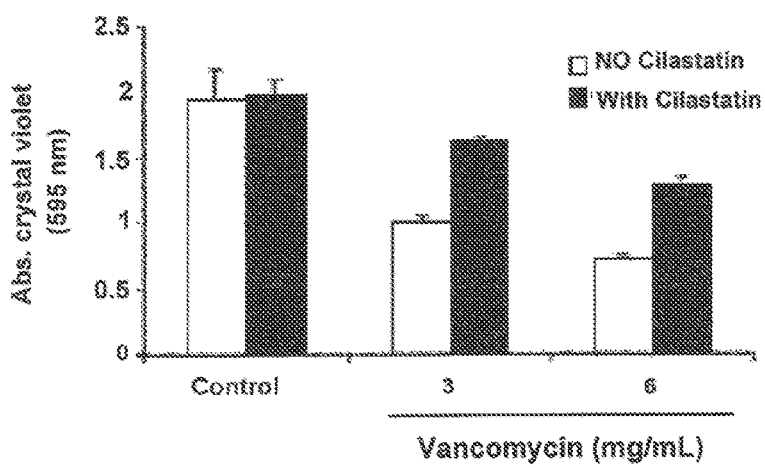
Figure 8C:
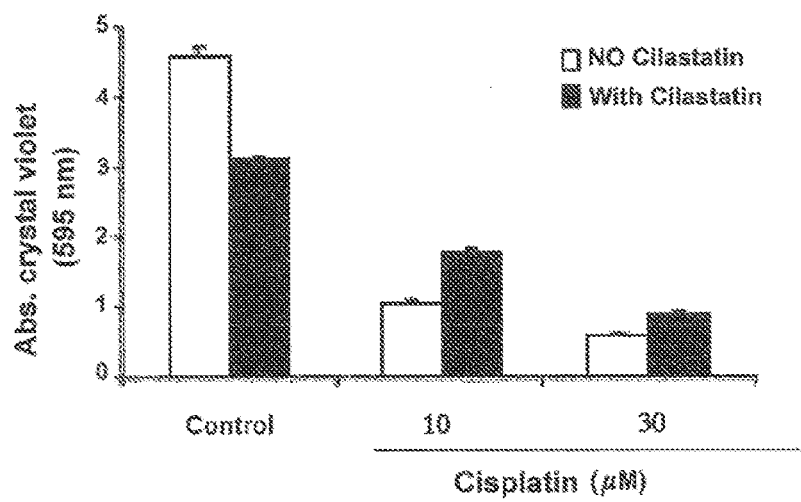
Figure 8D:
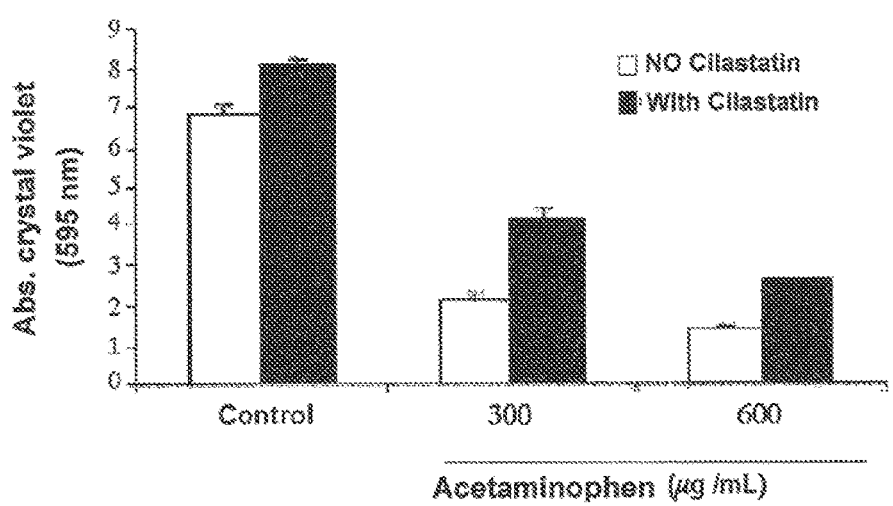
Figure 8E:
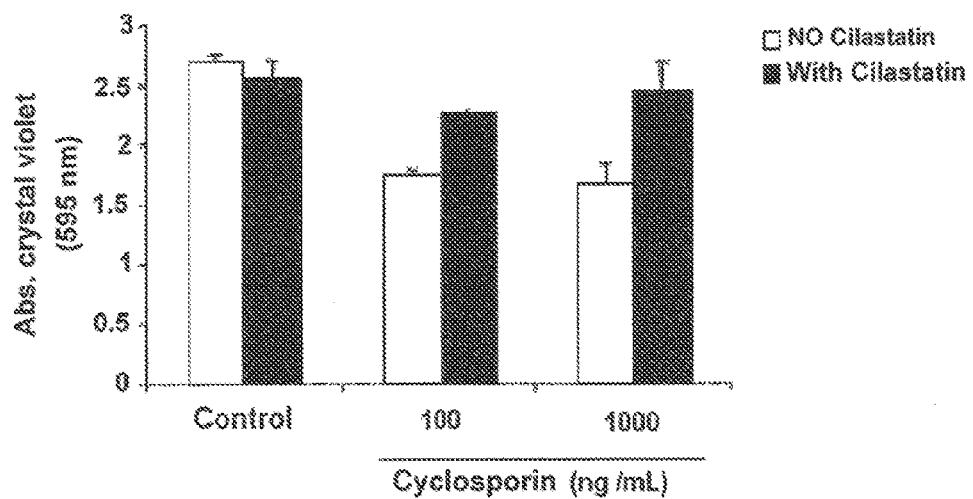
Figure 8F:
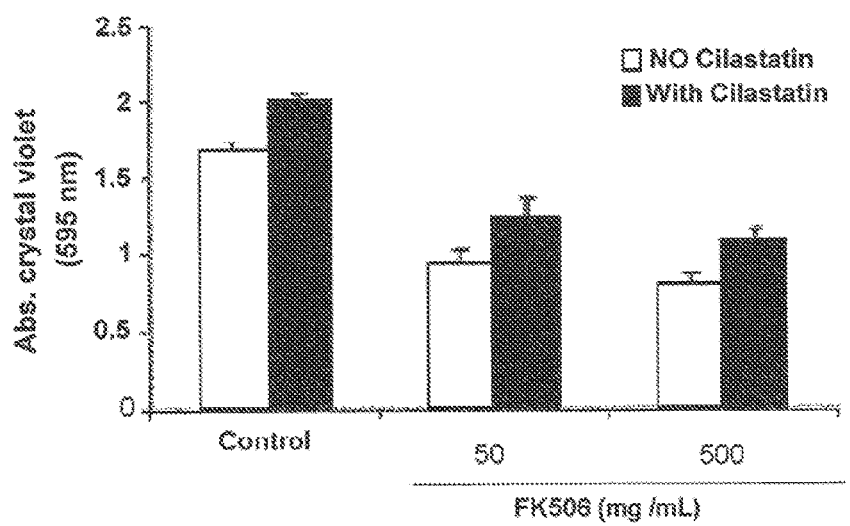

FIGS. 8A-8F show the results of tests of formation of surviving colonies, potential formers of regeneration colonies, detected by staining with crystal violet of cultured cells treated with each of the nephrotoxics indicated below the graphs, in the presence and absence of cilastatin. An improved cell recovery from nephrotoxic aggression, with an increased long-term survival (7 days), could be seen following co-administration of cilastatin and the nephrotoxics indicated below the graphs. FIG. 8A: gentamicin (in this case, and as an example for all others, photographs of the dishes where cells surviving aggression appear stained with crystal violet are shown); FIG. 8B: Vancomycin. FIG. 8C: cisplatin, FIG. 8D: acetaminophen, FIG. 8E: cyclosporin; FIG. 8F: tacrolimus (FK506). Graphs show the results obtained from measurement of absorbance at 595 nm of the stain of proximal tubular cells incubated for 24 hours with the nephrotoxics indicated in each case, at the concentrations given below the bars, after cell staining with crystal violet. The first bar of each pair corresponds to incubation in the absence of cilastatin (white bars), and the second bar to incubation in the presence of cilastatin (black bars).

Figure 9:
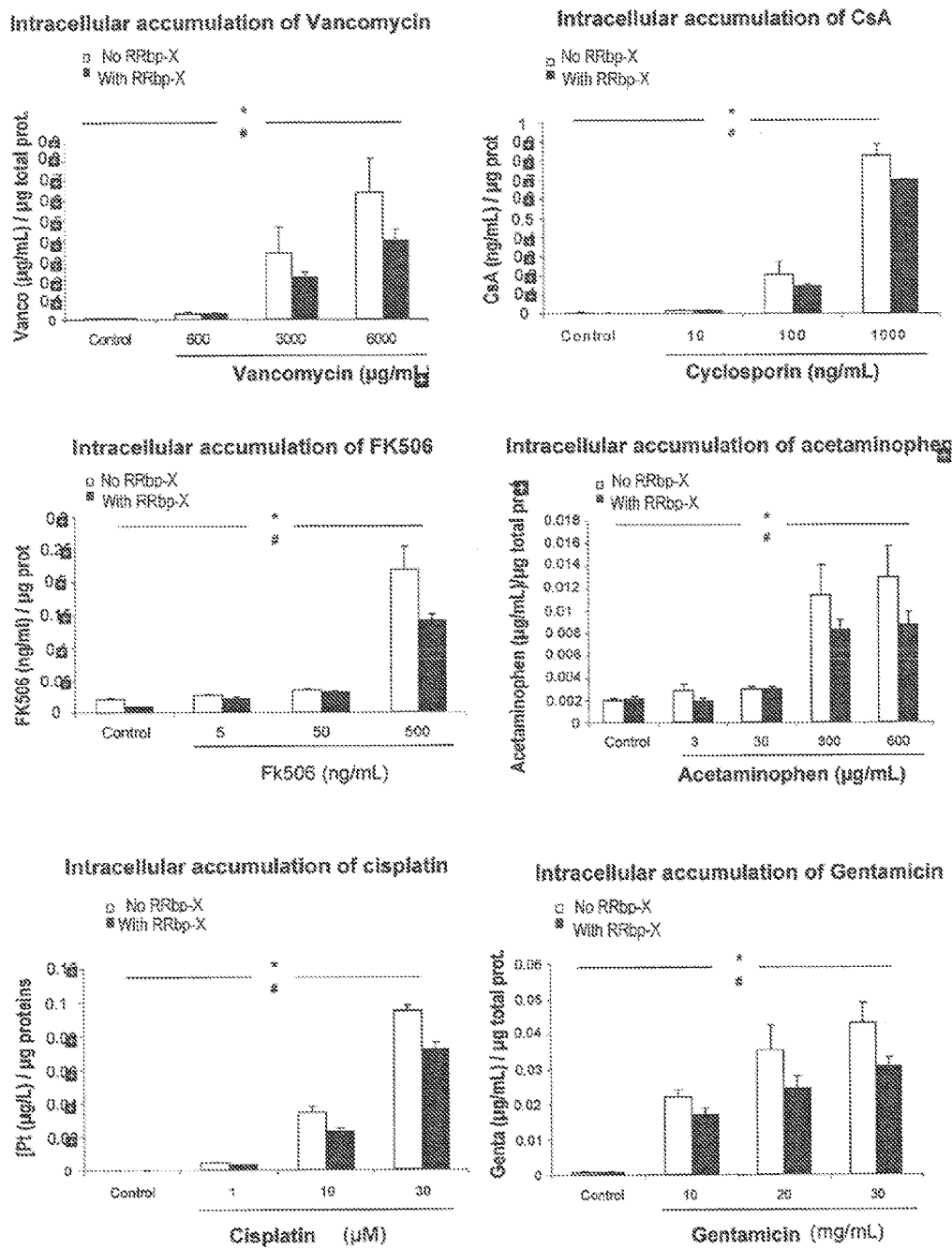

FIG. 9 shows intracellular accumulation of various nephrotoxics (from left to right: vancomycin, cyclosporin, tacrolimus (FK506), acetaminophen, cisplatin, and gentamicin) when primary cultures of proximal tubular cells were exposed for 24 hours to increasing concentrations of nephrotoxics in the absence (white bars) or in the presence (black bars) of cilastatin (RRbp-x). Cilastatin was shown to prevent entry of nephrotoxics into the proximal cell. *: cilastatin effect p<0.05; #: dose effect p<0.05.

Figure 10A:
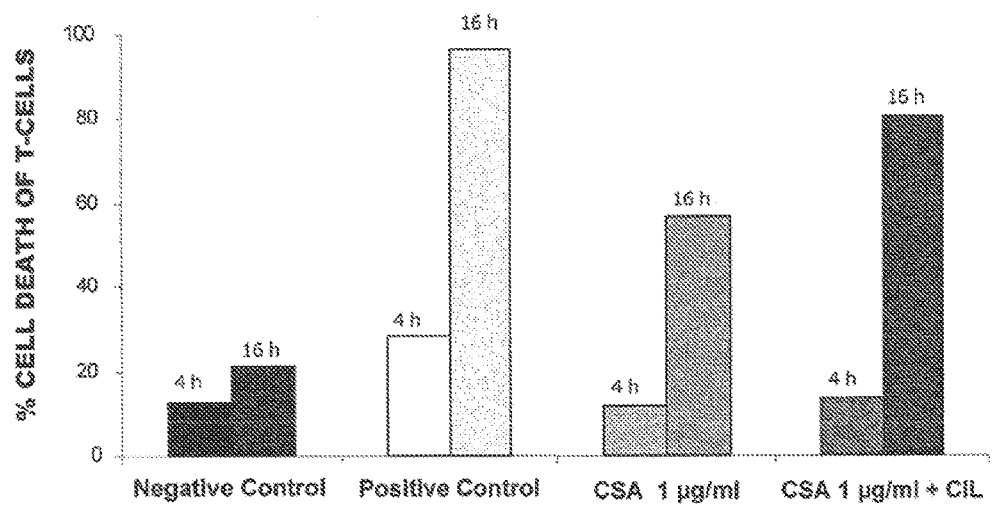
Figure 10B:
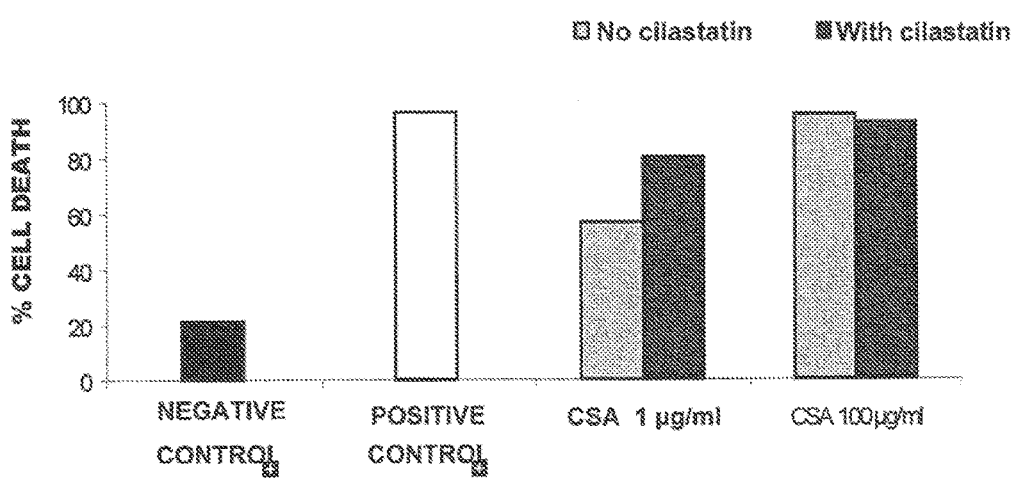

FIGS. 10A and 10B show that the nephroprotective effect of cilastatin is specific for the proximal tubule. The absence of a protective effect of cilastatin (RRbp-X) upon induction of cell death induced by cyclosporin A (CsA) is shown by representing the percent cell death seen in T cells (the target at cyclosporin A) incubated in the absence of treatment ("negative control") or incubated with camptothecin ("positive control"), cyclosporin A ("CsA"), or cyclosporin A+cilastatin. FIG. 10A shows the increase over time in percent cell death caused by CsA in the studied period: after 4 hours of incubation (first bar of each pair) or after 16 hours of incubation (second bar of each pair). FIG. 10B depicts the dose-response effect of the lethal effect of CsA on human T cells, shown by the differences found on incubation with different doses of CsA. This figure shows the absence of the protective effect of cilastatin (RRbp-X) on cell death induction by cyclosporin (CsA) by representing the percent cell death seen in lymphocytes incubated in the absence of treatment ("negative control") or incubated with camptothecin ("positive control"), cyclosporin at 1 µg/mL (third pair of bars) or cyclosporin at 100 µg/mL (fourth pair of bars). The absence of a protective effect in the presence of cilastatin is seen (second bar of the third and fourth pair of bars).

Figure 11A:
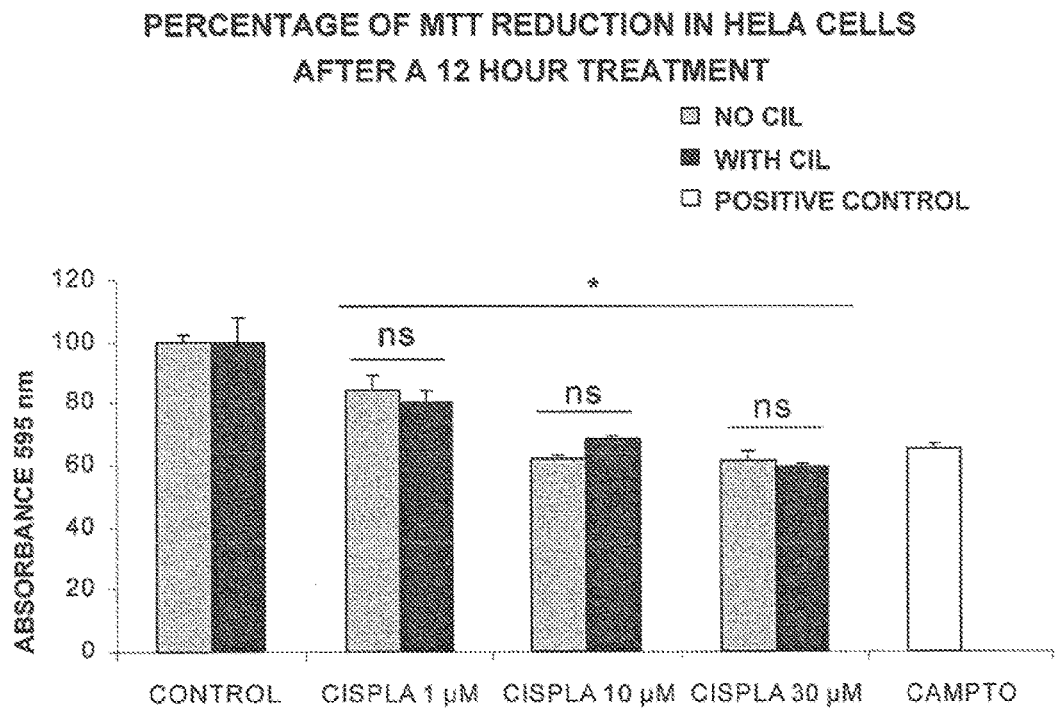
Figure 11B:
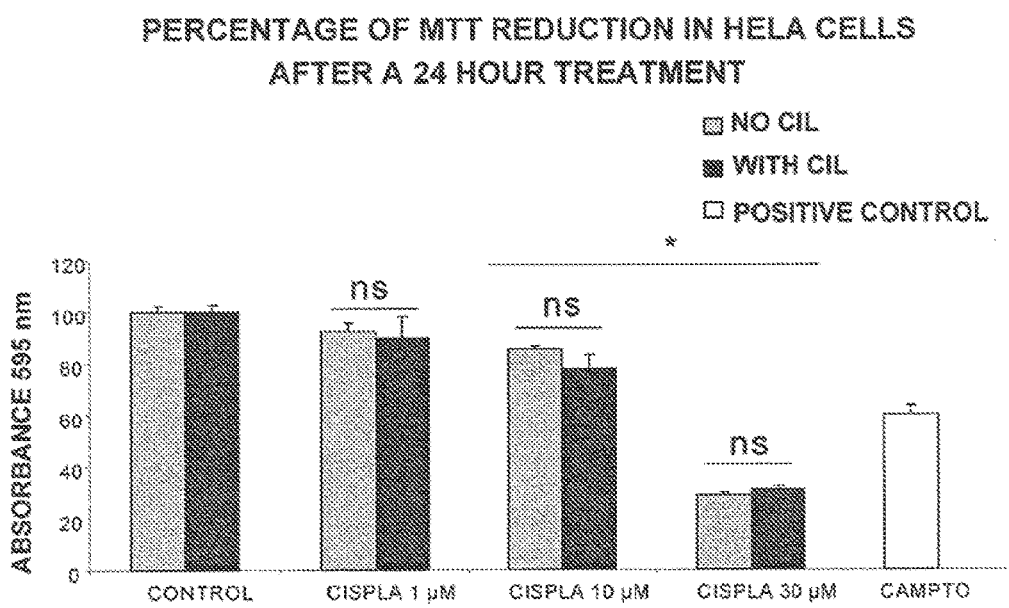

FIGS. 11A and 11B also show that the nephroprotective effect of cilastatin is specific for the proximal tubule. The effect of cisplatin on mitochondrial activity in HeLa tumor cells (the target of cisplatin), obtained from the absorbance values at 595 nm measured in the cells after conducting the MTT reduction test after incubation for 12 hours (FIG. 11A) or 24 hours (FIG. 11B) with the compounds indicated below the bars, is shown. Control: untreated cells, incubated with culture medium alone; CISPLA: cell incubated with cisplatin at concentrations of 1 µM (second pair of bars in each graph), 10 µM (third pair of bars in each graph), or 30 µM (fourth pair of bars in each graph); CAMPTO: camptothecin, positive control for death from apoptosis. Each of the treatments was carried out in the absence of cilastatin (first bar of each pair: bars filled grey, "NO CIL") or in the presence of cilastatin (second bar of each pair: bars filled black, "WITH CIL"). *p≤0.05 vs. control and control+cilastatin; ns=not significant.

Figure 12A:
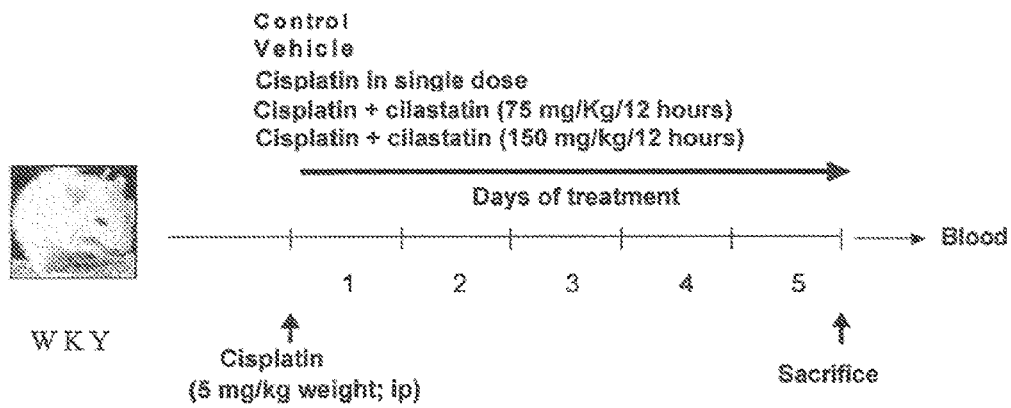
Figure 12B:
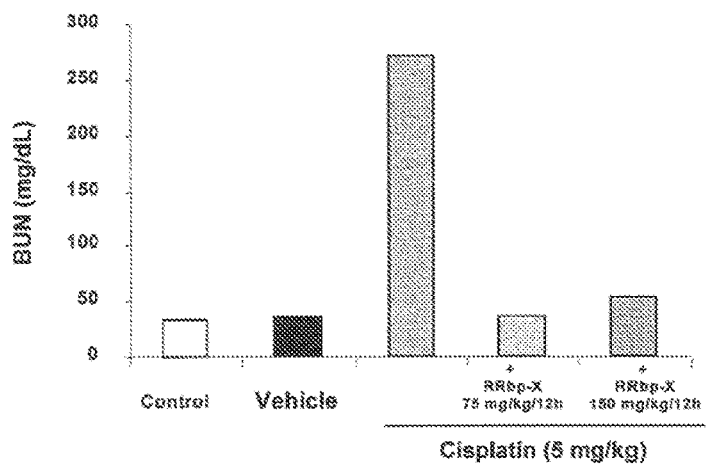
Figure 12C:
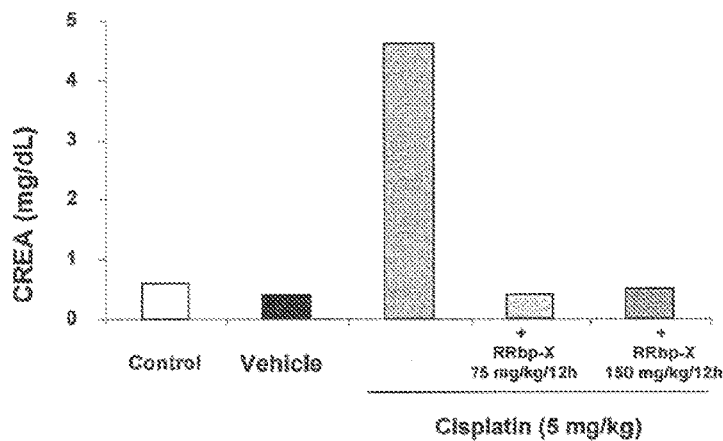

FIGS. 12A-12C refer to a preliminary in vivo test (Wistar rats) conducted to verify that the nephroprotective effect of cilastatin could be observed in vivo. The study was specifically designed to show nephroprotection by cilastatin against acute toxic renal failure caused by cisplatin.

FIG. 12A shows a scheme of the administration regimen of cisplatin and cilastatin given to the animals.

FIGS. 12B and 12C respectively show the values of BUN (blood urea nitrogen) and creatinine (CREA), both given in mg/dL, measured in blood serum of 5 animals observed: Cisplatin+cilastatin (RRbp-X) 75 mg/kg/12 h: animal with intraperitoneal injection of cisplatin (5 mg/kg/body weight, dissolved in saline)+cilastatin (RRbp-X)—dissolved in saline—at a dose of 75 mg/kg body weight every 12 hours by the intraperitoneal route from the day of cisplatin administration and until the day of killing; cisplatin+cilastatin (RRbp-X) 150 mg/kg/12 h: animal with intraperitoneal injection of cisplatin (5 mg/kg/body weight, dissolved in saline)+cilastatin (RRbp-X) at a dose of 150 mg/kg body weight every 12 hours in the same regimen and formulation as above; cisplatin: animal with intraperitoneal injection of cisplatin (5 mg/kg/body weight, dissolved in saline) plus saline every 12 hours at the same volumes and regimens as for the groups treated with cilastatin; vehicle: animal treated with saline at the same volumes and regimens as if it was treated with cisplatin and cilastatin; control: animal with no injection or treatment.

Figure 13A:
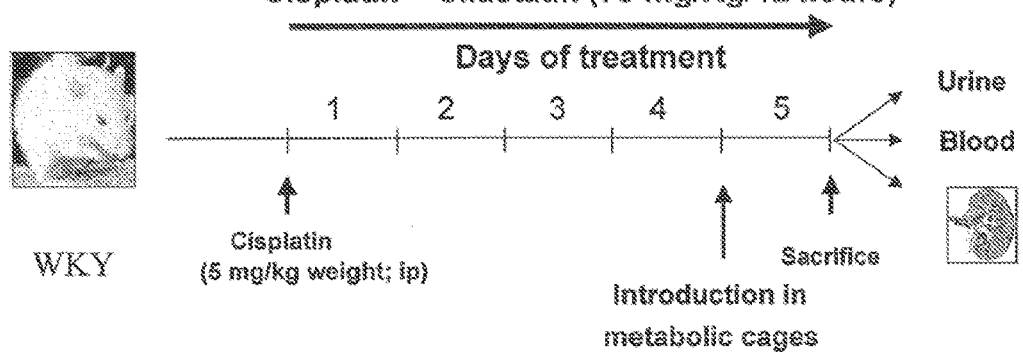

FIGS. 13A-13E refer to a second nephroprotection study, also conducted in vivo (Wistar rats), intended to confirm the nephroprotective effect of cilastatin against acute toxic renal failure caused by cisplatin:

FIG. 13A shows a scheme of the administration regimen of cisplatin and cilastatin given to the animals.

Figure 13C:
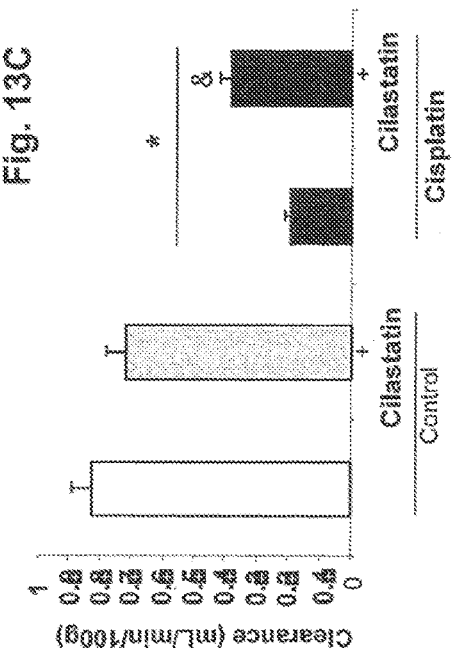
Figure 13E:
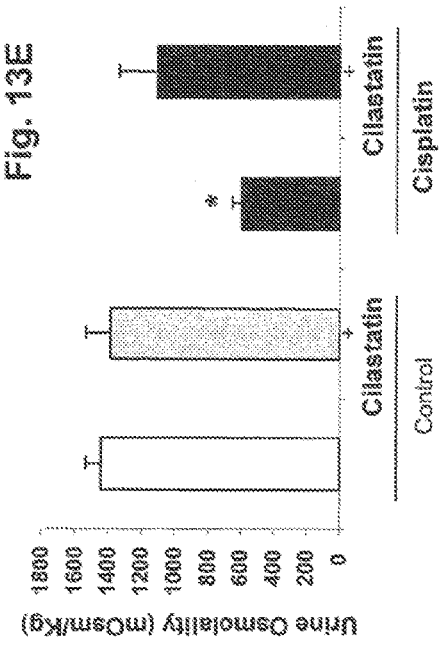
Figure 13B:
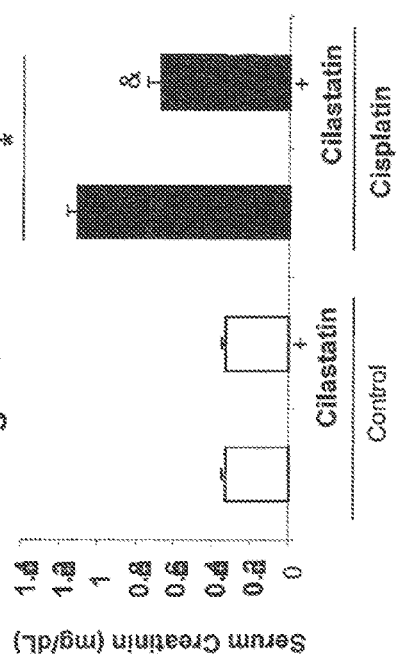
Figure 13D:
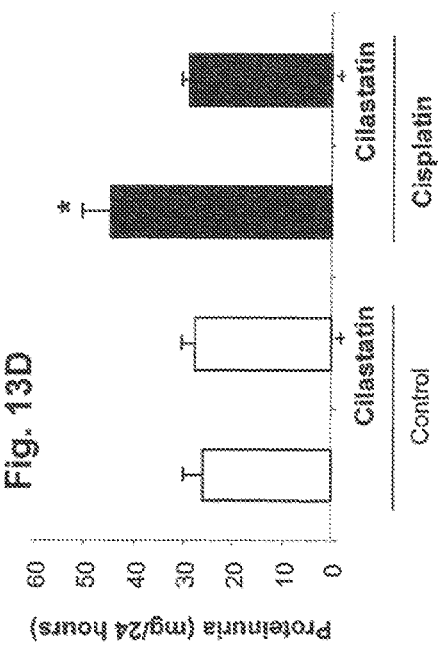

FIGS. 13B, 13C, 13D, and 13E respectively show the values of serum creatinine (mg/dL), renal clearance (mL/min/100 g), proteinuria (mg/24 hours, and osmolality (mOsm/kg) measured in samples from the 4 groups of animals under observation: Control (treated with saline alone) (white bars with no filling), control+cilastatin (animals given cilastatin dissolved in saline at doses of 75 mg/kg body weight every 12 hours by the intraperitoneal route from the day of cisplatin administration and until the day of killing) (white bars with dark stippled filling); cisplatin (animals with intraperitoneal cisplatin injection (5 mg/kg body weight, dissolved in saline) plus saline every 12 hours at the same volumes and regimens as for cilastatin-treated groups) (bars with solid black filling); cisplatin+cilastatin (animals with intraperitoneal cisplatin injection (5 mg/kg body weight, dissolved in saline) plus cilastatin dissolved in saline at 75 mg/kg body weight every 12 hours by the intraperitoneal route from the day of cisplatin administration and until the day of killing) (bars with black filling and white stippling). In FIGS. 13B and 13C: *: P<0,0001 vs. control and control+cilastatin; &: P≤0.005 vs. cisplatin. In FIGS. 13D and 13E, *: P≤0.005 vs. all other groups.

Figure 14:
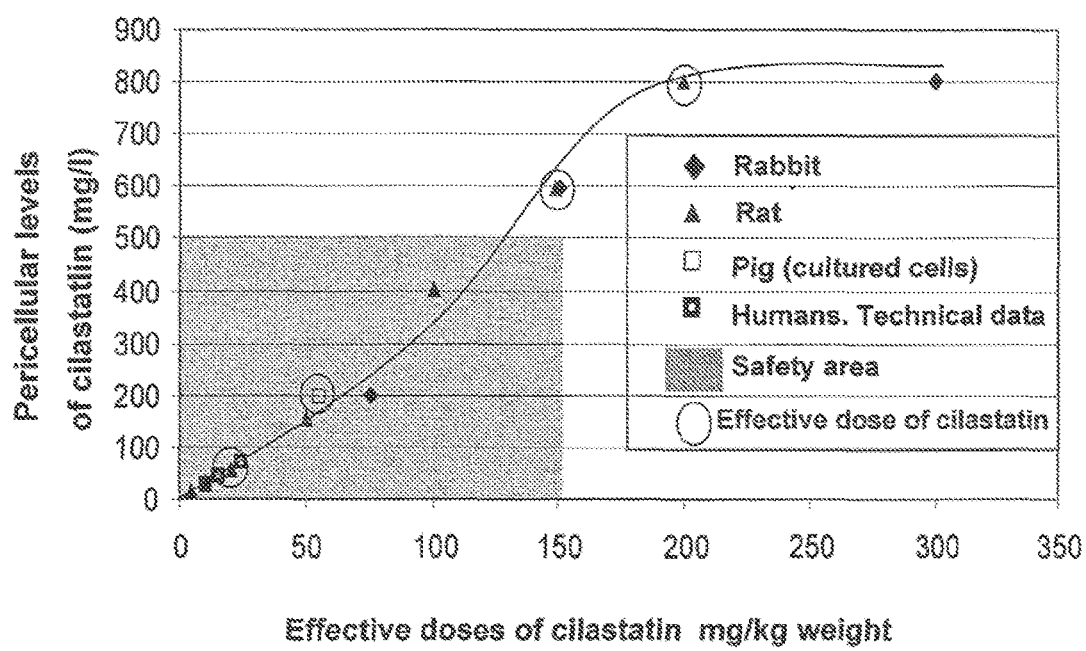

FIG. 14 shows a diagram derived from the specifications in the cilastatin summary of product characteristics, animal tests, tests in cells in culture, and references to other animal models. The diagram relates the effective cilastatin doses given, in milligrams per kg body weight (mg/kg) (data in the X-axis), to pericellular cilastatin levels, given as milligrams per liter (mg/L) in the Y-axis. Symbols: diamonds (♦): rabbit data; triangles (▲): rat data; blank squares ( ): data from experiments conducted with cultured pig cells; filled squares with a central point (⊡): data from the summary of product characteristics of the commercial product for humans containing cilastatin. The shaded box represents the safety area derived from pericellular concentration data (pig). Symbols surrounded by circumferences represent the doses at which cilastatin efficacy is shown in this report.

EXAMPLES

The following experimental products and procedures were used for the Examples described below:
Nephrotoxics and nephroprotector (cilastatin)
Cyclosporin A: Purchased from Sandoz (Novartis), Sandimum (solution for injection).
Tacrolimus: Purchased from Astellas, Prograf (solution for injection).
Gentamicin: Purchased from Guinama (powder)
Vancomycin: Purchased from Combino Pharm (powder).
Cisplatin: Purchased from Pharmacia (solution for injection).
Acetaminophen: Purchased from Bristol-Myers Squibb, Perfalgan, (solution for injection).
Amphotericin B: Purchased from Bristol, Fungicina (powder).
Chloroform: Purchased from Scharlau (liquid solution).

Mannitol: Purchased from Braun, Osmofundina (20% mannitol) (solution for injection).

Foscarnet: Purchased from AstraZeneca, Foscavir (solution for injection).

Iodinated contrast (iopamidol): Purchased from Rovi, Iopamiro (solution for injection).

Cilastatin: Purchased from Merck, Sharp & Dohme (powder).

Primary cultures of cells from the proximal tubular epithelium Primary cultures of cells from the proximal tubular epithelium were obtained from kidneys of miniature pigs of the Maryland strain. These pigs have been genetically selected for organ transplant studies and are homozygous for three loci of the major histocompatibility complex (MHC) (Sachs et al, 1976). Animals came from the specialized farm of the Aranjuez Farming Complex held by the Madrid regional government for animal experimentation purposes.

Animals selected for this study had a mean age of 3 months and a mean weight of 31.3 ±0.7 kg, and no distinction was made between males and females.

Animals used were handled at all times in accordance to the applicable legal regulations (Royal Decree 1205/2005 of October 10, 252/2005) by staff trained in the management of experimental animals and under the supervision of the veterinary surgeon in charge.

Twelve hours before surgery, animals were fasted and given water ad libitum. Animals were premedicated 15 minutes before surgery with ketamine 10 mg/kg body weight and atropine 0.025 mg/kg IM. Once sedated, animals were transferred to the operating table, placed in a supine position, anesthetized with an induction dose of propofol 10 mg/kg IV, and intubated. During surgery, anesthesia was maintained with nitrogen peroxide/oxygen (4 L/min NO2 and 2 L/min O2), Diprivan® (Propofol) 15 mg/kg/h, Fentanest® (Fentanyl) 0.75 mg/20 min, and Pavulon® (pancuronium bromide) 2 mg/20 min. Animals were killed using an anesthetic overdose and potassium chloride (KCl).

Kidneys were removed in the operating room under sterile conditions by bilateral simple nephrectomy through a transperitoneal approach. Once removed, kidneys were immediately transferred to HAM'S-F12 (Bio-Whittaker) with penicillin (100 IU/ml) and streptomycin (100 µg/ml) (Bio-Whittaker) at 4° C.

To isolate proximal tubules, the cortex was dissected and sectioned under a laminar flow hood (Gelaire Flow laboratories, modelo BSB 3A) using a Steadie-Riggs microtome (Tomas Scientific, USA) Sheets were gassed with carbogen and digested with collagenase A (Sigma) (30 mg/kidney), diluted in HAM'S F12 (50 mL/kidney, final collagenase concentration 0.6 mg/mL), for 20 or 30 minutes under stirring (150 rpm) at 37° C. This process was monitored to prevent excess digestion, removing the tissue when turbidity was seen in the medium and the edges of tissue sheets appeared disintegrated.

After stopping digestion with cold HAM'S, the digested material was filtered through a 250 µm metallic mesh (ENDECOTTS LTD.). The filtrate was washed three times with HAM'S-F12 in a centrifuge (Sorvall GLC-2B, tilt rotor) at 150 g for one minute to remove collagenase residues. Tubule content in the final sediment was 80%. In order to increase purity and remove contaminants, this was processed through a 45% isotonic Percoll gradient (Pharmacia) in Krebs-bicarbonate buffer (NaCl 112 mM, KCl 3.3 mM, $PO_4H_2K$ 1.2 mM, $MgSO_4.7H_2O$ 1.2 mM, $CaCl_2$ 0.5 mM, 95% $O_2$/5% $CO_2$) and centrifuged at 20000 g for 30 min (RC-5B, Refrigerated superspeed Centrifuge, Rotor SS-34). Proximal tubules (Tejedor 1988) with a purity higher than 98% are found in lane 4.

Tubules were collected with a sterile Pasteur pipet and were washed three times with cold HAMS-F12 with penicillin (10000 IU/mL) and streptomycin (10000 µg/mL) at 150 g to remove Percoll. The precipitate obtained was weighed to determine the yield.

For obtaining the primary culture of proximal tubular cells (PTCs), tubules were diluted at a concentration of 0.66 mg of tubules/mL of culture medium (CM): HAM'S-F12/DMEM (Dulbecco's Modified Eagles's Medium with 1 g/L glucose, Bio-Whittaker) in a 1:1 ratio, supplemented with HEPES 25 mM, glutamine 2.5 mM, 1% non-essential amino acids, penicillin 100 U/mL, and streptomycin 100 µg/mL, 2% fetal calf serum (FCS) (Bio-Whittaker), sodium bicarbonate 20 mM (MERCK), hydrocortisone $5 \times 10^{-8}$ M, insulin 5 µg/mL, transferring 5 µg/mL, and selenium 5 ng/mL (SIGMA).

Five milliliters of this suspension were distributed in each dish (Corning, 60 mm in diameter). Dishes were kept in an incubator (Heraeus) at 37° C. with 5% $CO_2$. The first change of medium was not made until the fourth day, to allow cell adhesion to the dish. From that day, the medium was changed every 2-3 days. Cells reached confluence at 8-10 days, and signs of senescence started to occur at 12-13 days.

Cell Growth Dynamics

Cultured cells were counted in situ on images of the cell monolayer obtained in a microscope in a 40× field, calibrated using a Neubauer grid and corresponding to 0.0775 $mm^2$. Images were acquired using a videomicroscopy system (COHU camera coupled to a computer through a VG-5 video recording card with integration chip) that allowed for rapid image recording, so that cells were returned to the incubator after a short time period. Images were analyzed using Scion Image software (Scion Corporation, 1998), based on the Image deMcIntosh software of the National Institute of Health, USA.

In each culture, each tested treatment was applied to a minimum of six dishes. Each dish was assigned a number and was divided into seven sectors, six peripheral and one central. Dishes were selected using a random number table (Epiinfo) for taking images at the specified times. Three dishes of the corresponding treatment were selected, and seven images were taken from each of them, one from each sector. The mean value of the 21 counts was considered as the value n−1 for the corresponding day and treatment. The "n" given in the corresponding experiments represents the number of animals studied for each condition, and the measures of change correspond to the errors of the means between animals for the tested condition.

Confocal Microscopy

To study cilastatin, interaction with CRs, cholera toxin B conjugated with a fluorophore (FICT, supplied by Molecular Probes) that uses such rafts for its cell internalization was employed. Two modifiers of cholesterol rafts were also used as negative controls: cyclodextrin, supplied by Sigma Spain, and filipin, supplied by Calbiochem.

Primary cultures of PTCs were pre-incubated with cyclodextrin (CDX) (1 mM), filipin (50 µg/mL), cilastatin (200 µg/mL), or culture medium alone (controls) for 20 minutes. These were subsequently incubated with cholera toxin B-FITC (10 µg/ml) at different times (1 hour and 2.5 hours). Cells were washed with PBS and fixed with 4% formaldehyde at room temperature for 5 minutes. Samples were mounted in an inverted position on slides with a drop of DAKO Fluorescent mounting medium and were observed in the confocal microscope.

Nucleosome enrichment: Release of oligonucleosomal DNA to the cytosol To quantify oligonucleosomes present in the cytosol of cultures of proximal tubular cells treated for 48 h with the nephrotoxic compounds selected (cyclosporin A, gentamicin, tacrolimus (FK506), vancomycin, cisplatin, iodinated contrast, foscarnet, mannitol, amphotericin B, chloroform, and acetaminophen) in the presence or absence of cilastatin, the enzymoimmunoassay kit for death cell Cell Death Detection ELISA$^{PLUS}$ (Boehringer Mannheim), that determines oligonucleosomes with antihistone-biotin and anti-DNA-peroxydase antibodies, was used.

The previously described proximal tubular cells were cultured to confluence in plates of 24 wells 16 mm in diameter, subjected for 48 h to the corresponding treatments, and lysed with 200 μL of lysis solution for 30 min at room temperature. The lysate was collected and centrifuged at 200 g for 10 min (Eppendorf 5417C). From the resulting supernatant (cytosolic fraction), 20 μL were added to each of the streptavidin-coated wells of the ELISA plate, adding a mixture of anti-histone-biotin antibodies (which recognize the streptavidin in the plate bottom and histone proteins in DNA) and anti-DNA-peroxydase antibodies (which recognize DNA; peroxydase performs the colorimetric reaction allowing for quantification), and incubating 2 hours at room temperature.

Once incubation had occurred, wells were washed, ABTS (a peroxydase substrate) was added, and activity was measured photometrically at 405 nm with an Anthos 2020 plate reader. The relationship between the enzymatic activity of a sample incubated for a given time period and the corresponding value at time 0 hours after activation (enrichment factor) was calculated.

Assessment of Mitochondrial Activity Using MTT

Mitochondrial functionality of PTCs was measured by metabolic reduction of 3-(4,5-dimethylthiazole-2-yl)-2,5-diphenyltetrazole bromide (MTT, supplied by Calbiochem), performed by the mitochondrial enzyme succinate dehydrogenase, yielding a blue-colored compound (formazan). Cells were seeded into 96-well plates, grown to semiconfluence, and subjected to their corresponding treatments for 24 hours. MTT was subsequently added to each well at a final concentration of 0.5 mg/mL and incubated for 3 hours at 37° C. in the dark. Once this incubation was completed, 100 μL of lysis buffer (20% SDS in 50% N,N-dimethylformamide, pH 4.7) were added, and the plate was incubated overnight at 37° C. in the dark. Absorbance was measured at 595 nm on the following day.

Percent viability was calculated as follows:

$$\% \text{ Viability} = \frac{OD \text{ treated cells} \times 100}{OD \text{ control cells}}$$

Real time MTT reduction was measured in semiconfluent proximal cells seeded in 24-well plates (16 mm in diameter) in which culture medium was replaced by MTT at 0.5 mg/mL of final concentration in PBS. This reduction was determined by measuring absorbance at 595 nm with an Olympus 1×70 inverted fluorescence microscope coupled to a photomultiplier controlled from a SLM Aminco 2000 fluorimeter. Two measurements were made in the first test (with vancomycin), one control to quantify the amount of MTT reduced by the cells in the absence of the toxic and one incubation with vancomycin 25 mg/mL for 20 min. In the second test (cisplatin, acetaminophen, cyclosporin, and tacrolimus), the same measurements were done, but in this case, instead of incubating with the toxic, the latter was directly added to the plate during absorbance recording. In this test, a third recording was added in which MTT reduction was measured in proximal cells treated with vancomycin at the same concentration as previously and with cilastatin 200 μg/mL from the start of recording. In this test, as in the previous ones, vancomycin was directly added to the plate during measurement of absorbance.

Viability of proximal tubular cells: flow cytometry Subconfluent primary cultures of PTCs, subject to the corresponding treatments for 24 hours, were used. Cells shed to the supernatant were collected by direct aspiration using an automatic pipet, and adherent cells were separated from the culture plate by trypsinization.

The PTCs thus obtained were separately fixed and permeabilized with 70% ethanol and stored at −20° C. After removing ethanol, cells were washed two times with PBS. They were subsequently incubated with PBS-EDTA, propidium iodide (PI) 40 μg/mL, and RNAse 250 μg/mL for 45 minutes in the dark and at room temperature.

The count was performed in a FACScan cytometer (Beckton Dickinson) equipped with a simple argon ion laser. Windows were fixed based on the characteristics of FSC (size), SSC (complexity), FL2-H (height), FL2-A (area), and FL2-W (width). The latter two were used to rule out cell doublets. Analysis was performed using WinMDI 2.9 software.

Scanning Electron Microscopy

Scanning electron microscopy studies were carried out at the Department of Pathology of Gregorio Marañon General University Hospital.

For scanning microscopy techniques, plastic coverslips 25 mm in diameter (Nunc) were placed in the base of culture plates. After the corresponding treatment, cells were fixed with 1% glutaraldehyde in PBS for one hour, washed and incubated for 24 hours at 4° C. with 1% osmium tetroxide in PBS in a 1:1 ratio. After removing osmium tetroxide, samples were dehydrated with acetone, sequentially increasing its proportion from 50% to 100% in 30-minute passages and mounted on an aluminium support and shaded with gold (Fine Coat Ion Sputter JFC-1100 JEOL). Finally, photos were taken using a JEOLJSM-T300 scanning microscope.

Colony formation test using crystal violet staining Cells were seeded in 6-well plates to semiconfluence and were treated for 24 hours with the corresponding toxics in the presence and absence of cilastatin. Cells were subsequently detached with trypsin and washed with sterile saline to remove residues of stimuli. Cells were re-seeded in 100-mm Petri dishes with 10% FCS medium and grown for 7-10 days. After this time, culture medium was removed from the dishes, which were fixed for 5 minutes with 5% paraformaldehyde in PBS and stained for 2 minutes with crystal violet (0.5% crystal violet in 20% methanol). Once stained, cells were washed twice with PBS 1× and were photographed. After taking the photographs, crystal violet was eluted with 2 mL of eluate solution (50% ethanol and 50% 0.1 M sodium citrate, pH 4.2). Eluate absorbance was quantified in an ELISA reader at 595 nm.

Total Protein Extraction and Quantification of Intracellular Concentration of Toxics in PTCs Subconfluent primary cultures of PTCs were subjected to treatment with the different nephrotoxics tested for 24 hours. After incubation, culture medium was discarded, adding 400 μL of lysis buffer (2.2% (w/v) SDS; 19.33% (v/v) 87% glycerol (v/v); 790 mM Tris HCl pH 6.8, 50 mL) per 100-mm diameter dish at 70° C. Cells were subsequently detached, and the final volume obtained was recorded. Cell lysate was subjected to a thermal shock, for which it was first heated at 100° C. for 5 min and then placed on ice. Each sample was subjected to sudden decompression. Samples were centrifuged, at 12000 rpm for 5 min, and supernatant was collected. Protein concentration was measured using the Bradford method (Bradford 1976), and samples were stored at −2° C. until use.

Intracellular accumulation was measured in lysates of cells treated with nephrotoxics, in the presence or absence of cilastatin, using fluorescence polarization immunoassay (TDX) (ABBOTT Laboratories, USA) according to manufacturer instructions, except for cisplatin, whose intracellular concentration was measured using mass spectrometry with inductive coupling plasma ICP-MS Termo X-Series (Termo Electron, Windsford, Cheshire, United Kingdom) monitoring isotopes $^{195}$Pt, $^{194}$Pt, and $^{191}$Ir.

Cell Viability in Lymphocytes

CD3+ lymphocytes isolated from peripheral blood, separated by immunomagnetism from healthy donors after obtaining their informed consent (cell samples courtesy of Dr. Buño. Department of Bone Marrow Transplant (Gregorio Marañon Hospital), were used to assess the potential interaction of cilastatin in lymphocytes treated with CsA. The sample was centrifuged at 120 g and was resuspended in 750 μL of RPMI medium (in the absence of FCS: fetal calf serum) to quantify the number of cells available using trypan blue. One hundred thousand cells per point were distributed.

Lymphocytes were incubated in RPMI (Bio-Whittaker) with no treatment (negative control), with CsA, with cilastatin, with both, and finally with camptothecin (Sigma) as positive control for death from apoptosis. Incubation was performed for 4 hours at 37° C. Cells were centrifuged for 6 minutes at 1200 rpm. The precipitate was resuspended in 100 μL of buffer (10 mmol/L HEPES, 150 mmol/L NaCl, 5 mmol/L KCl, 1 mmol/L Mg Cl$_2$, 1.8 mmol/L CaCl$_2$) and 5 μL of annexin-V. It was incubated in the dark for 10 minutes.

Intensity of green fluorescence of cells was quantified as displacement in the logarithmic scale from control (cells growing in 10% FCS) versus the number of cells analyzed. Cell debris was excluded from the analysis.

Apoptosis was also determined in lymphocytes at 16 hours by adding higher doses, 100 μg/mL and 1000 μg/mL, to the previous ones.

Cell Viability in Tumor Cells (HeLa)

Cisplatin is another drug for which it is extremely critical to discern whether the nephroprotection provided by cilastatin is associated or not with a reduction in drug potency.

To ascertain that cisplatin did not lose antitumor cytotoxic activity in the presence of cilastatin, the drug was tested on a tumor cell line such as HeLa cells. The procedure use for conducting the tests was the previously described assessment of mitochondrial activity using MTT. The procedure was carried out at 12 and 24 hours with cisplatin doses of 10 and 30 μM. Camptothecin 50 μg/mL was used as positive control. The presence or absence of cilastatin (200 μg/mL) resulted in no change in its cytotoxic effect.

Experimental in vivo Model of Cilastatin Nephroprotection Against Acute Toxic Renal Failure Caused by Cisplatin: A Preliminary Study For the preliminary in vivo study on cilastatin protection against cisplatin-induced renal aggression, male Wistar rats with a mean weight of 290±20 g and a mean age of 8-9 weeks, bred and kept at the animal house of the Section of Experimental Medicine and Surgery of Gregorio Marañon General University Hospital, were used.

Animals were handled at all times according to the applicable legal regulation in Royal Decree 1201/2005, of October 10, on the protection of animals used for experimentation and other scientific purposes, under the direct supervision of the veterinary surgeon in charge.

Five animals, each subjected to a different treatment regimen, were preliminarily used. Two of the animals did not receive cisplatin (control and vehicle), while the other three animals were administered a single intraperitoneal injection of cisplatin dissolved in saline at a dose of 5 mg/kg body weight. Among the three animals given cisplatin, one also received cilastatin (RRbp-X) dissolved in saline by the intraperitoneal route, at a dose of 150 mg/kg body weight every 12 hours, from the day of cisplatin administration to the day of killing. Another animal treated with cisplatin received cilastatin (RRbp-X) in the same regimen and formulation, but at a dose of 75 mg/kg body weight every 12 hours. The last animal treated with cisplatin received saline (cilastatin vehicle) in the same regimen and formulation as in the previous two groups. Among animals not treated with cisplatin, one was administered saline in the same volumes and regimens as in the other three groups (vehicle), while the other animal did not receive any puncture or treatment (control) (FIG. 12A).

As may be seen in FIG. 12A, the study lasted 5 days for intraperitoneal administration of cisplatin or saline in the case of the vehicle animal, and throughout the period animals were given free access both to water and feed (standard diet) under controlled light, temperature, and humidity environmental conditions. At the time of killing, animals were weighed and anesthetized with ketamine (10 mg/kg) and diazepam (4 mg/kg). Once anesthetized, blood was drawn by cannulation of the abdominal aorta at the bifurcation level. This blood was kept for 30 minutes at 37° C. and subsequently for 1 hour at 4° C, after which it was centrifuged at 2000 rpm for 15 minutes at 4° C. This allowed for separation of blood serum, which was stored at −80° C. until use.

In vivo Experimental Model of Nephroprotection by Cilastatin Against Acute Toxic Renal Failure Caused by Cisplatin Study on Wistar Rats For the in vivo experimental model of cilastatin protection against cisplatin-induced renal aggression, male Wistar rats with a mean weight of 260±15 g and a mean age of 7-8 weeks, bred and kept at the animal house of the Section of Experimental Medicine and Surgery of Gregorio Marañon General University Hospital, were used.

Animals were handled at all times according to the applicable legal regulations in Royal Decree 1201/2005, of October 10, on the protection of animals used for experimentation and other scientific purposes, under the direct supervision of the veterinary surgeon in charge.

Two weeks before the experimental animal model was started, animals were weighed, identified by numbers, and separated into different cages based on the study groups. Animals were watched and weighed several times before the start of the study to ascertain their evolution.

A total of 28 animals were used, which were randomized into 4 groups with a sample size n=6-8 animals per group. The study groups and their treatments were therefore as follows (FIG. 13A).

Cisplatin+Cilastatin group (n=8): animals with a single intraperitoneal administration of cisplatin (5 mg/kg/body weight), dissolved in saline, +cilastatin (dissolved in saline) at a dose of 75 mg/kg body weight every 12 hours by the intraperitoneal route from the day of cisplatin administration and until the day of killing.

Cisplatin group (n=8): animals with a single intraperitoneal administration of cisplatin (5 mg/kg/body weigh), dissolved in saline, every 12 hours in the same volumes and regimens as groups treated with cilastatin.

Control+Cilastatin group (n=6): animals treated with intraperitoneal administration of saline (cisplatin vehicle) in the same volume as cisplatin-treated groups, plus cilastatin (dissolved in saline) at a dose of 75 mg/kg body weight every 12 hours by the intraperitoneal route from the day of administration of saline (cisplatin vehicle) and until the day of killing.

Control group (n=6): animals treated with saline in the same volumes and regimens as the groups treated with cisplatin and/or cilastatin.

As may be seen in FIG. 13A, the study lasted 5 days from intraperitoneal cisplatin administration (in the cisplatin and cisplatin+cilastatin groups) or saline (in the control and control+cilastatin groups). From that time, cilastatin (in the control+cilastatin and cisplatin+cilastatin groups) or its saline vehicle (in the cisplatin and control groups) were co-administered every 12 hours. Throughout the period, animals were given free access to both water and feed (standard diet) in a controlled light, temperature, and humidity environment. One day before killing, animals were introduced into metabolic cages with free access to feed and water ad libitum to collect 24-hour urine, in order to quantify urine output and protein concentration. Proteinuria was measured using the sulphosalicyclic acid method (Gyure, 1977) and was expressed as mg of protein/24 hours.

At the time of killing, animals (previously weighed) were anesthetized in the experimental operating room with ketamine (10 mg/kg) and diazepam (4 mg/kg) and were drawn blood by cannulation of the abdominal aorta at the bifurcation level. Blood was first incubated for 30 minutes at 37° C., and then for one hour at 4° C. Subsequent centrifugation at 2000 rpm for 15 minutes at 4° C. allowed for obtaining blood serum, which was frozen at −80° C. until use. After exsanguination, the aorta was clamped to cut its flow above the kidneys, the inferior vena cava was perforated, and kidneys were perfused through the cannula with cold saline (Braun Medical S. A., Barcelona, Spain). Kidneys were subsequently removed, decapsulated, and kept in cold saline during their handling to minimize tissue degradation. Kidneys (right and left) were weighed and were subsequently handled similarly. Right kidneys were cross sectioned just above the renal artery, and their upper renal poles were introduced into 4% paraformaldehyde in PBS for 24 hours for their subsequent fixation and paraffin embedding. The rest of the right kidneys, as well as left kidneys, were separated into cortex and medulla, and both samples were frozen in liquid nitrogen and stored at −80° C. until use.

Samples of the heart, liver, and aorta were also taken from the animals, and were adequately processed and stored at −80° C.

Renal samples immersed in paraformaldehyde were fixed for 24 hours at 4° C. They were subsequently dehydrated with increasing ethanol concentrations and finally embedded in paraffin in the Histolab ZX tissue processor (Especialidades Medicas MYR SL, Tarragona, Spain) for morphological and immunohistochemical studies.

Hemodynamnic variables and serum and urine kidney function parameters (FIG. 14) were measured using a Dimension RxL autoanalyzer from Dade-Behring according to manufacturer instructions.

Statistical Analysis

—In vivo experiments

All tested variables of interest were quantitative continuous variables, and their values are given as the mean±standard error of the mean. All measurements were performed in duplicate, and each result provided was obtained in at least three preparations from different animals. When singular tracings are shown, similar results have been obtained in at least two additional occasions.

Effects of cilastatin on the variables modified by the nephrotoxic drugs tested were analyzed using factorial repeated measures tests. Results were analyzed using a general two-way ANOVA model for independent measures. The two usual factors in each study were the "cilastatin factor", with two levels (yes, no), and the "toxic dose" factor, usually with four levels corresponding to the doses (in such a case, the test was controlled with a "0" dose in the first factor level). The models mentioned always included the "cilastatin*toxic dose" interaction factor, as well as an a posteriori analysis of the differences between levels, using the LSD (least significant difference) test as a discriminating test. A two-sided $\alpha=0.05$ was considered significant. When significant differences were found for the cilastatin protection factor, an attempt was made to confirm such difference by comparison of the non-linear adjustments of the corresponding dose-responses.

In the event of outliers, separation from the median by more than two interquartile ranges was considered as non-inclusion criterion.

—In vivo experiments

A Levene test was used to calculate equality of variances between the groups. Continuous variables showing equal variances and a normal distribution were analyzed using an ANOVA test, while a Kruskal-Wallis test was used for variables not meeting these requirements. Results are given as mean±standard error of the mean. Values of $p \leq 0.05$ were considered significant. SPSS software was used for all statistical tests performed.

Example 1

Reduction of Internalization of Cholesterol Rafts by Cilastatin Interaction with DHP-I This test was conducted to show whether cilastatin, through its interaction with DHP-I, anchored to cholesterol rafts (CRs) by a GPI group, could block transport through CRs or interfere with the CR-dependent endocytic pathway.

For this, caveolae were identified on cells of pig proximal tubular epithelium in primary culture obtained as described above. One of the proteins in the caveola, the cholera toxin B receptor, was used for this purpose. By adding fluorescent toxin B, labeled with a fluorophore (FITC), caveolae are labeled and their fate over time may be followed using confocal microscopy.

Figure 1A:
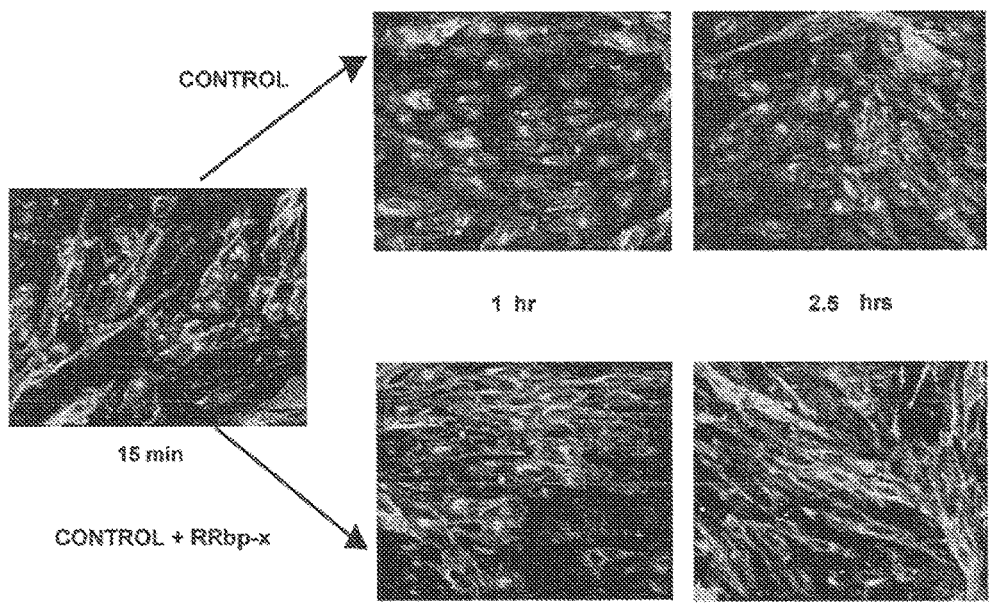

The results obtained are shown in FIG. 1A. At 15 minutes, fluorescent staining was seen alone all cell membranes, regardless of treatment.

Evolution of fluorescence in the absence of cilastatin may be seen in the upper part of the image: after one hour, fluorescence starts to accumulate in a perinuclear position, in the region corresponding to Golgi apparatus: at 2.5 hours, Golgi staining is evident, while disappearance of staining from cell membranes is seen.

The lower part of FIG. 1A shows the same cells incubated in the presence of cilastatin (RRbp-X). As may be seen, at 2.5 hours labeled caveolae had not moved from the cell membrane.

Figure 1B:
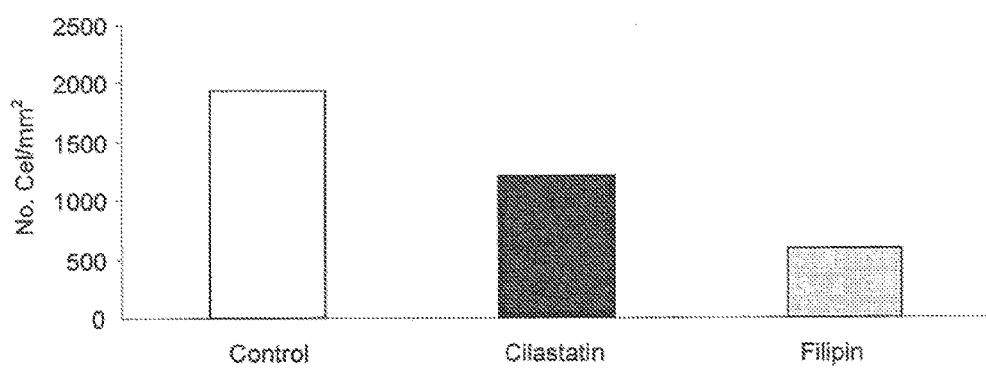

FIG. 1B shows the observable reduction in labeling in the Golgi apparatus 2.5 hours after cell membrane caveolae were labeled with fluorescent toxin B in the presence of cilastatin or filipin. Destruction of caveolae with filipin prevents their internalization. However, filipin causes cell death in a short time. Cilastatin also presents localization of caveolae labeling in the Golgi apparatus. But it does it through its binding to renal DPH-I.

Example 2

Safety of Cilastatin

Some of the early studies on cilastatin prior to its marketing stated that cilastatin, at a dose of 1 g/kg/day, could cause sloughing of tubular endothelium as a sign of renal toxicity (Sack 1985).

Figure 2:
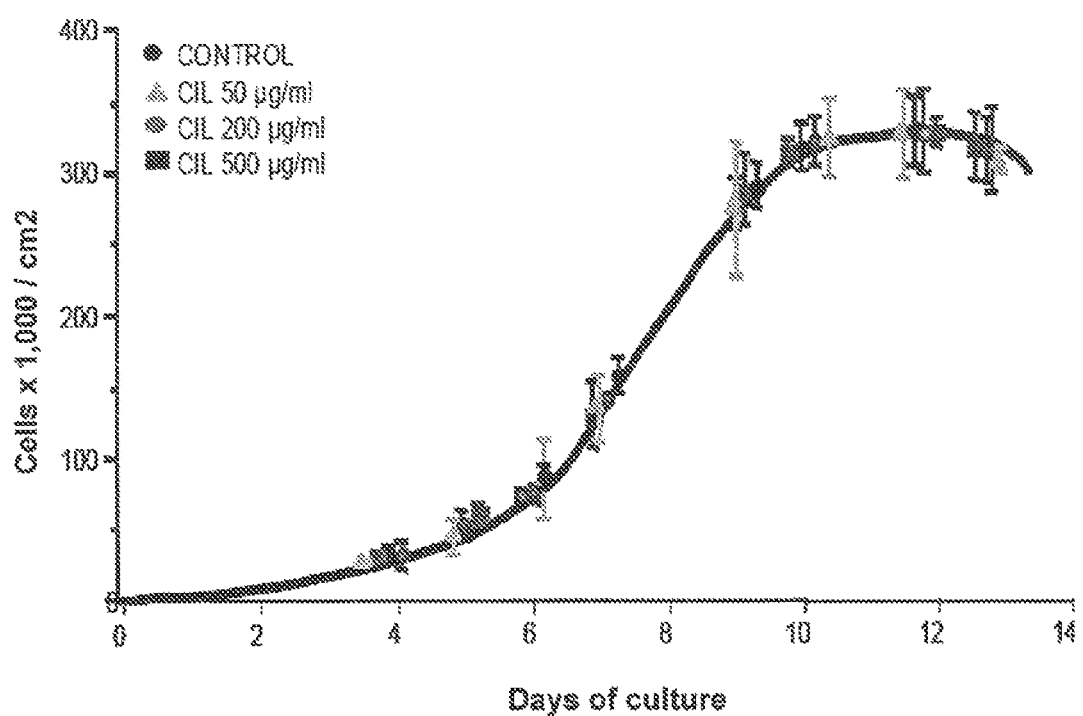

To verify this, an in vitro study was conducted on primary cultures of proximal tubular cells (PTCs) incubated in the presence of increasing cilastatin doses for a total of 14 days. Cultured cells were counted as previously discussed in the section "Cell growth dynamics". Results are shown in FIG. 2. where the different cilastatin concentrations used are given.

No significant effect was seen upon growth dynamics, cell confluence, or monolayer morphology. Concentrations used were up to almost 10 times the plasma concentrations reached in vivo.

Example 3

Cilastatin Abolishes or Reduces the Damage Caused to the Proximal Tubule by the Main Nephrotoxics 3.1.—Cilastatin prevents or reduces cell apoptosis During apoptosis, endogenous endonucleases break down DNA into oligonucleosomes which pass to the cytoplasm, where they stay for several hours before becoming part of the blebs or apoptotic corpuscles. Occurrence of these oligonucleosomes may be interpreted as a manifestation of the apoptitic process.

To assess the protection provided by cilastatin against nephrotoxicity caused by different nephrotoxics, the above described "nucleosomal enrichment" methodology was used, quantifying appearance of DNA fragments in the cytosol as a manifestation of the apoptotic process.

Primary cultures of proximal tubular cells were incubated against a battery of 11 nephrotoxic drugs: cyclosporin A (immunosuppressant), gentamicin (aminoglycoside antibiotic), tacrolimus (FK506) (immunosuppressant macrolide), vancomycin (glycopeptide antibiotic, cisplatin (anticancer drug), iodinated contrast (iopamidol), foscarnet (antiviral), mannitol (diuretic), amphotericin B (antifungal), chloroform, and acetaminophen (analgesic and antipyretic). None of the drugs tested is a DPH I substrate; some of them are anionic and may reach the inside of the cell through OATs, but others are neutral or even cationic. Some are lipid-soluble and other water-soluble, as previously indicated in Table 1 of this report. The intracellular transport mechanism is generally unknown for most of them, and it is assumed that they diffuse freely through the cell membrane.

Figure 3:
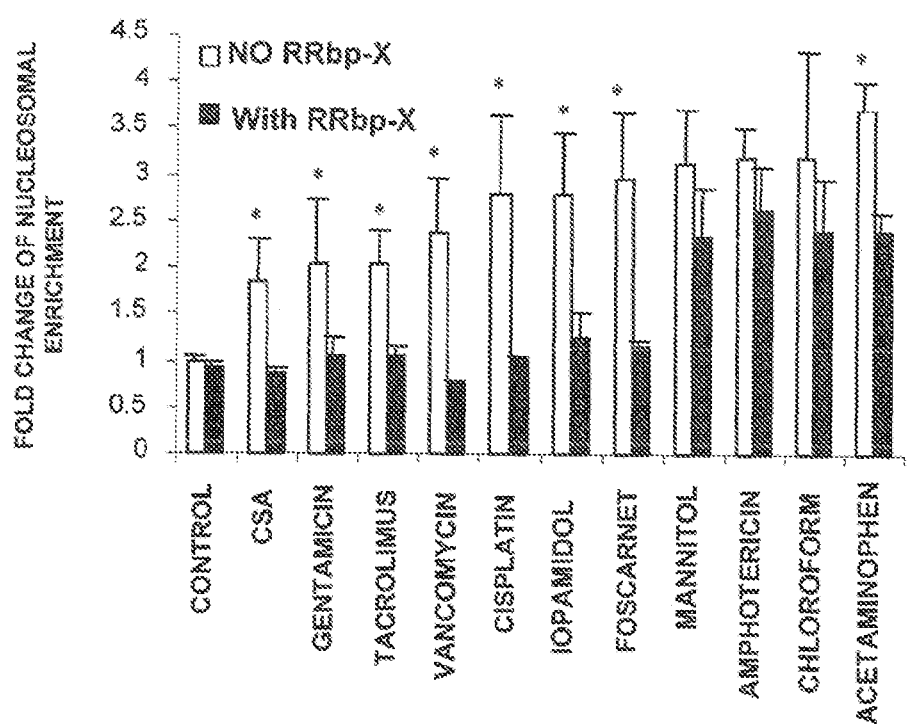

The results obtained in the primary cultures incubated with the nephrotoxics and when primary cultures are co-incubated with the same nephrotoxics plus cilastatin (RRbp-X) are shown in FIG. 3. The figure shows that an increase occurs, as compared to control, in quantification of nucleosomes for all tested toxics. When primary cultures are co-incubated with the same nephrotoxics plus cilastatin, induction of apoptosis ceases or is significantly reduced. In many cases, a return occurs to a situation similar to baseline.

3.2.—Cilastatin prevents or reduces cell death by anoikis

Toxic or ischemic aggression to the tubule results in a type of cell death associated to sloughing of damaged cells, a process known as anoikis.

Induction of anoikis by the tested nephrotoxics may be measured by quantifying the number of cells moving from the monolayer to the culture supernatant by flow cytometry, which was done in this case using the previously described procedure for calculating the viability of proximal tubular cells.

Addition of cilastatin (RRbp-X) to cultures reduced in all cases the number of dead cells.

The graphic representation in FIG. 4A shows all values corresponding to cell counts in the supernatant for all tested conditions and doses, representing incubations without cilastatin in the X-axis and incubations with cilastatin (RRbp-X) in the Y-axis. If cilastatin had no protective effect, cells sloughed by anoikis in both axes would be identical, and all points would fall on the identity line. However, it may be seen that for all tested conditions, toxics, and doses the points fall on the protection line: Much less cell death occurs in the presence of cilastatin.

As an example, FIG. 4B shows the flow cytometries of the supernatants from primary cultures of proximal tubular cultures incubated with two potent nephrotoxics, cisplatin or vancomycin, in the absence or presence of cilastatin (RRbp-X). FIG. 4C shows quantification of cells sloughed to the supernatant with progressive doses of four nephrotoxic drugs (vancomycin, gentamicin, cisplatin, and acetaminophen) and the reduction in their number induced by co-incubation with cilastatin (RRbp-X) (dark grey bars) An ANOVA for repeated measures (overall cilastatin effect=0.012) and a post hoc analysis (cilastatin effect on each drug: $p<0.05$) were performed.

3.3.—Cilastatin restores the mitochondrial oxidative capacity of the proximal tubule Both oligonucleosome accumulation and the anoikis phenomenon are late events in the process by which the tested compounds induce toxic damage in the proximal tubular cell.

The mitochondrion of the proximal tubule is probably the earliest organelle altered during apoptotic cell death. Mitochondrial impairment frequently occurs some hours before the mechanisms finally leading to DNA fragmentation (the previously discussed nucleosome formation) and cell sloughing from the monolayer (anoikis) are triggered. Therefore, study of mitochondrial function in relation to the nephrotoxics assessed may be of value for understanding the latency of the protection phenomenon. This was made by measuring the activity of the mitochondrial oxidative chain through electron transfer to 3-(4,5-dimethylthiazole-2-yl)-2, 5-diphenyltetrazolium bromide (MTT, from the abbreviated form methyl-thiazoletetrazolium) bromide, which on reduction is converted into insoluble blue formazan crystals.

The results obtained for the different nephrotoxics are shown in FIGS. 5A-5E, both with regard to MTT reduction after treatments for 24 hours with each of the nephrotoxics and real time results.

The results of the ANOVA tests performed were as follows:
  vancomycin: vancomycin effect not significant, cilastatin effect $p=0.025$, "interaction" effect (vancomycin+cilastatin) not significant;
  cisplatin: cisplatin effect $p=0.038$, cilastatin effect $p=0.001$, "interaction" effect (cisplatin+cilastatin) not significant acetaminophen: acetaminophen effect p=0.05, cilastatin effect not significant, and "interaction" effect (acetaminophen+cilastatin) not significant As may be seen, the nephrotoxics tested caused a dose-dependent inhibition of mitochondral electronic transfer in all cases. The presence of cilastatin totally or partially restores such capacity.

Example 4

Cilastatin Restores the Morphology and Regenerative Capacity of Tubular Epithelium Damaged by Nephrotoxics 4.1.—Cilastatin restores cell morphology Images of electron scanning microscopy, obtained following the previously described methodology, showed the appearance of cultures of cells of the proximal tubular epithelium incubated for 11 days in the presence of 1 μg/mL of cyclosporin A or the same concentration of cyclosporin but in the presence of 200 μg/mL of cilastatin.

FIG. 6 shows some examples of the photographs obtained. The two images on the left show how cyclosporin A causes cytosolic condensation, cell rupture, and monolayer disruption, characteristic of the apoptosis it induces. In the images on the right, two photographs of epithelium exposed to the same doses of cyclosporin A, but in the presence of cilastatin (RRbp-X), it may be seen how these changes do not usually occur in the presence of cilastatin, though occasional apoptotic blebs may be seen to also appear in its presence.

4.2.—Cilastatin improves cell recovery following aggression

To verify whether cilastatin had any effect upon cell recovery, a new experiment was made in which the dynamics of cell growth in primary cultures of proximal tubular cells was tested in the presence of two nephrotoxic drugs, cyclosporin A and tacrolimus (FK-506), checking the differences in the presence and absence of cilastatin.

As shown in the graphs in FIGS. 7A and 7B, when cells in culture were grown, from the time of seeding, in the presence of cyclosporin A (1 or 10 μg/mL) or tacrolimus (50 ng/mL), cell growth was dose-dependently reduced.

Thus, these tests show that co-incubation with the nephrotoxic and cilastatin (200 μg/mL) partially prevents the effect of nephrotoxics on cell growth, protecting from their nephrotoxicity.

Results of statistical analysis were as follows:

Factorial ANOVA N=5: Combined effects: $p<0.0001$; "treatment" factor: $p<0.0001$; "culture days" factor: $p<0.0001$; "treatment×culture days" factor: $p<0.0004$.

A post hoc analysis for cyclosporin showed a significant decrease in cilastatin-induced cell growth as compared to control from day 8 (dose of 1 μg/mL and dose of 10 μg/mL) and a cell growth recovery with cilastatin from day 11.

A post hoc analysis for tacrolimus (FK-506) showed a significant decrease in cell growth from day 7, with a recovery from the same time with cilastatin.

To confirm these data, another method for testing the regenerative capacity of cells after an aggression was used: the number of colony-forming units was determined by staining with crystal violet, a dye that requires cell integrity to be incorporated into the cells. This procedure has the advantage that it allows for gross visualization of the intensity of aggression, and also for quantification of aggression if cells are resuspended and the dye is determined by visible spectrophotometry. Thus, in in vitro nephrotoxicity studies on cultured cells, crystal violet staining serves for detecting surviving cells, potential colony formers in regeneration.

FIGS. 8A-8E show some examples of measurement of colony-forming units 24 hours (12 hours for cisplatin) after an aggression with increasing doses of several nephrotoxics in the absence or presence of cilastatin (RRbp-X). This test confirms that co-incubation with cilastatin totally or partially restores cell growth inhibited by the nephrotoxic, because the test showed that an improved cell recovery, with an increase in long-term survival (7 days), occurred in cases where the nephrotoxic was coadministered with cilastatin.

Example 5

Cilastatin Prevents Entry of Nephrotoxics into the Proximal Cell Due to its Effect on the Brush Border Previous examples have shown how the presence of cilastatin in culture media prevents or greatly reduces induction of apoptosis of the anoikis phenomenon, restores mitochondrial oxidative capacity, and increases the number of cells surviving to the different nephrotoxic aggressions, which increases the resistance to aggression and the regenerative capacity of the renal tubule.

All toxics tested have different physico-chemical characteristics and different intracellular targets. None of them is a substrate for DHP-I, and had not been reported to date to use any common cell entry pathway. The effect described in this report about the capacity of cilastatin to inhibit cycling of proximal tubule caveolae could be the substrate for the broad spectrum nephroprotective effect shown by this drug.

To confirm that this new hypothesis was true, cilastatin had to be shown to interfere with intracellular accumulation of all drugs tested. For this purpose, PTCs were incubated with the different nephrotoxics under study, and the cumulative intracellular concentration of toxics in PTCs was quantified, in accordance with the procedure described at the start of the Examples.

The results obtained with vancomycin, cyclosporin, tacrolimus (FK506), acetaminophen, cisplatin, and gentamicin are shown in FIG. 9, in which the different progressive concentrations of each of these nephrotoxics to which cells were exposed may also be seen.

According to these results, suggesting that cilastatin interferes with intracellular administration of all nephrotoxics tested, cilastatin appears to be able to inhibit an intracellular nephrotoxic accumulation pathway not known to date as such, as a result of its binding to renal dipeptidase-I.

Example 6

The Broad Spectrum Nephroprotective Effect of Cilastatin is Specific for the Proximal Tubule Cell protection strategies against drugs of clinical value but with a recognized specific toxicity, based on drug transport blockade, are not usually clinically applicable because the protective agent also often blocks entry of the damaging drug into its own cell target.

However, the specificity conferred to cilastatin action by its targeting of a protein that is only located in the cholesterol rafts of the proximal tubule allows for assuming that it will have no protective effect on cells having no brush border (and hence no DPH-I).

The accumulated experience with the I/C combination, an antibiotic widely used in the most diverse clinical conditions with no reports of a reduction in the pharmacological activity of other drugs concomitantly administered, supports this assumption. None of the authors describing the interaction between I/C and CsA reported or mentioned an increased risk of rejection associated to the interaction, which appears to suggest that T cell death induced by CsA is not modified by cilastatin, which was confirmed by the authors of the invention who noted that cilastatin does not protect the T cell from the lethal effect of cyclosporin A. Tests were performed in accordance with the methods described in the section "Cell viability in lymphocytes", and results are shown in FIGS. 10A and 10B. Both the dose-response effect of the lethal effect of cyclosporin A on human T cells and the absence of a protective effect (percent cell death does not decrease) in the presence of cilastatin 200 µg/mL were seen.

Cisplatin is another drug for which it is extremely critical to discern whether the nephroprotection provided by cilastatin is associated or not with a reduction in drug potency. To ascertain that cisplatin did not lose its antitumor cytotoxic activity in the presence of cilastatin, cisplatin was tested on a tumor cell line (HeLa cells) following the method previously described in "Evaluation of mitochondrial activity using MTT", with the times and compound concentrations given in the section on "Viability in tumor cells (HeLa)". The presence or absence of cilastatin resulted in no change in the cytotoxic effect of cisplatin. Graphs with the percent reductions in MTT in HeLa cells after 12 and 24 hours of treatment are respectively shown in FIGS. 11A and 11B. The results given show that cilastatin (200 µg/mL) does not prevent the chemotherapeutic action of cisplatin in cancer cells (*p≤0.05 vs. control and control+cilastatin; ns=not significant.

Example 7

The Protective Effect of Cilastatin may be Observed In Vivo

In order to verify that in vivo nephroprotection actually occurred, two studies were done on Wistar rats as an experimental in vivo model of cilastatin nephroprotection against acute toxic renal failure caused by cisplatin, a preliminary model that provided the guidelines to be followed for a second wider experimental model, including more measurement variables. Rats received in both studies a single cisplatin dose and were monitored for 5 days.

7.1. Preliminary study

In the preliminary study, the effect of two parallel cilastatin administration regimens was verified as described in the section "Experimental in vivo model of cilastatin nephroprotection against acute toxic renal failure caused by cisplatin; a preliminary study". As stated in such section, study groups were as follows:

Cisplatin+cilastatin (RRbp-X) 75 mg/kg/12 h: animal with intraperitoneal injection of cisplatin (5 mg/kg/body weight, dissolved in saline)+cilastatin (RRbp-X)—dissolved in saline at a dose of 75 mg/kg body weight every 12 hours by the intraperitoneal route from the day of cisplatin administration and until the day of killing;

Cisplatin+cilastatin (RRbp-X) 150 mg/kg/12 h: animal with intraperitoneal injection of cisplatin (5 mg/kg/body weight, dissolved in saline)+cilastatin (RRbp-X) at a dose of 150 mg/kg body weight every 12 hours in the same regimen and formulation as above;—Cisplatin: animal with intraperitoneal injection of cisplatin (5 mg/kg/body weight, dissolved in saline) plus saline every 12 hours at the same volumes and regimens as for the groups treated with cilastatin;

Vehicle: animal treated with saline at the same volumes and regimens as if it was treated with cisplatin and cilastatin;

Control: animal with no injection or treatment.

These treatment regimens were followed for 5 successive days after initial administration of cisplatin or its vehicle (saline), after which animals were killed for obtaining blood serum.

A depiction of the administration regimens and the results obtained for blood urea nitrogen (BUN) and creatinine (CREA) in the preliminary study may be seen in FIGS. 12A-12C.

In the preliminary study, the animal receiving cisplatin alone lost 30% of its weight in 5 days and showed a significant elevation in plasma creatinine (see FIG. 12C). Animals treated with the same dose of cisplatin and with cilastatin showed no significant weight loss or changes in plasma creatinine.

Based on confirmation that the cisplatin dose used was able to cause renal dysfunction and that the two cilastatin doses used provided a similar protection (FIGS. 12B and 12C), the following study was designed, using several animals per group and testing more variables.

7.2. Extended study on Wistar rats.

Similarly, in the subsequent study (FIG. 13A) and also as described in the section (Experimental in vivo model of cilastatin nephroprotection against acute toxic renal failure caused by cisplatin: study on Wistar rats", the study groups, with their corresponding n, were as follows:

Cisplatin+Cilastatin group (n=8): animals with a single intraperitoneal administration of cisplatin (5 mg/kg/body weight), dissolved in saline, plus cilastatin (dissolved in saline) at a dose of 75 mg/kg body weight every 12 hours by the intraperitoneal route from the day of cisplatin administration and until the day of killing.

Cisplatin group (n=8): animals with a single intraperitoneal administration of cisplatin (5 mg/kg/body weight), dissolved in saline, every 12 hours in the same volumes and regimens as groups treated with cilastatin.

Control+Cilastatin group (n=6) animals treated with intraperitoneal administration of saline (cisplatin vehicle) in the same volume as cisplatin-treated groups, plus cilastatin (dissolved in saline) at a dose of 75 mg/kg body weight every 12 hours by the intraperitoneal route from the day of administration of saline (cisplatin vehicle) and until the day of killing.

Control group (n=6): animals treated with saline in the same volumes and regimens as the groups treated with cisplatin and/or cilastatin.

As in the previous study, these treatment regimens were administered for 5 successive days after initial administration of cisplatin or its vehicle (saline), after which animals were killed for obtaining blood serum. This time, urine samples were taken before killing, as indicated in the section describing the procedure.

FIG. 13A shows a representation of the administration regimens, while the results for creatinine, clearance, proteinuria, and osmolality in urine obtained from the second and more complete experimental model may be seen in FIGS. 13B to 13E). It may be seen that animals treated with cisplatin plus cilastatin had a significant partial decrease in creatinine and clearance values as compared to cisplatin-treated animals not receiving cilastatin, with their values been similar to control values. On the other hand, as regarded proteinuria and urinary osmolality, cilastatin completely reversed the values to normal levels as compared to those in animals who received cisplatin without cilastatin.

Table 3 gives data relating to weight loss.

TABLE 3

Body weight balance at the end of the extended study

| GROUP | BASELINE WEIGHT | FINAL WEIGHT | Δ WEIGHT |
|---|---|---|---|
| Control | 264 ± 3 | 279 ± 2 | 14.8 ± 1.3 |
| Control + Cil | 259 ± 8 | 273 ± 7 | 14.3 ± 1.5 |
| Cisplatin | 272 ± 4 | 249 ± 5 | −23.0 ± 2.9* |
| Cisplatin + Cil | 272 ± 5 | 259 ± 3 | −13.0 ± 3.7*& |

*$P \leq 0.0001$ vs. control and control + Cil.
&$P \leq 0.05$ vs. Cisplatin

Animals receiving cilastatin together with cisplatin experienced a clearly lower weight loss as compared to those given cisplatin alone. Thus, mean weight of control and control plus cilastatin animals increased by approximately 14 grams, while a significant weight loss occurred in the cisplatin-treated groups as compared to the former ($p<0.0001$). Animals given cisplatin and treated with cilastatin lost less weight than untreated animals, with a significant difference ($P<0.05$).

7.3 Extrapolation to humans of data obtained

In order to derive an effective dose that may be adequate in humans, available data from experimental animals on the relationship between the cilastatin doses administered, given in mg/kg body weight, and the cilastatin plasma levels achieved with them, given in mg/L, have been taken into account. Available data from rabbits (Toyoguchi 1997) and rats (Lin 1999 and Pérez 2004) and from the in vitro experiments reported here, in which pig cells were incubated in the presence of different cilastatin concentrations, have been used. No data have been reported for humans. Data from the summary of product characteristics of the medicinal product Tienam®, from Merck, Sharp and Dohme Spain S. A., manufactured by Abelló Farmacia S. L., (a product containing imipenem and cilastatin sodium) were therefore used to derive the corresponding human data (summary of product characteristics IPC 0195a, Tracer no. TEN/1V-E-14417, MOH modification-5/99 (6/99), available at http://www.msd.es/content/hcp/products/ft/ft_tienam_iv_500mg_es.pdf). Based on such data, a plot was drawn of the relationship between the dose administered and pericellular levels in mg/L: for studies performed in rabbits and rats, these pericellular levels were considered to be equivalent to the plasma levels detected for each administered dose: for the in vitro experiments conducted on pig cells, pericellular concentration would be the cilastatin concentration in the culture medium. The resulting plot is shown in FIG. 14 (diamonds: rabbit data; triangles: rat data; blank squares: data from pig experiments; filled squares including a white point: data from the summary of product characteristics for humans). In such plot, the shaded box represents the range of plasma levels (pericellular concentrations) at which cilastatin safety and absence of toxicity have been shown.

A linear relationship between the administered doses and the plasma levels achieved may be seen in the plot for all species. Such linearity is maintained up to doses of 200 mg/kg body weight and plasma levels around 800 mg/L. Above these figures, the relationship tends to be lost.

The circles surrounding some data represent the doses at which efficacy of the drug has been shown in this report. As may be seen, the minimum effective dose shown in studies discussed in this report corresponds to the therapeutic range proposed in the summary of product characteristics. Such dose may be estimated at 10 mg/kg body weight, which represents a mean value of 750 mg/day for a human adult. This is the estimated minimum nephroprotective dose in humans.

CONCLUSIONS

The results mentioned in the above Examples suggest that cilastatin has an unexpected and unknown effect upon the brush border of the proximal tubule, as a result of which it is able to prevent in variable degrees the nephrotoxicity of antibiotic, cytotoxic, anti-inflammatory, antiretroviral, anesthetic, and immunosuppressant drugs. Because of the difference in chemical structure, solubility in water or lipids, and ionic nature at physiological pH, it may be assumed that this nephroprotective effect may be extended to any drug, or compound with no known activity as a drug, able to damage the proximal tubule. This broad-spectrum nephroprotection is kidney-specific and does not interfere with the effects of the toxics concerned on their own targets. Cilastatin itself is devoid of toxic effects on proximal tubular cells. Cilastatin administration may therefore serve to reduce the nephrotoxic effects of drugs and other compounds with a nephrotoxic effect. Cilastatin administration may be concomitant and/or subsequent to drug administration. A single or several cilastatin doses may be administered, one of which may be given at the time of administration of the compound whose nephrotoxicity wants to be reduced.

LITERATURE REFERENCES

Adachi H, Tawaragi Y, Inuzuka C, Kubota I, Tsujimoto M, Nishihara T, Nakazato H. Primary structure of human microsomal dipeptidase deduced from molecular cloning. J Biol Chem 5;265(7):5 3992-3995 (1990).

Bagahie A, Bayat M, Abobo C et al. The effect of imipenem/cilastatin on acute cyclosporin nephrotoxicity in heart/lung transplant patients. Crit Care Med 23: A241 (1995)

Belitsky P, Ghose T, Girner M, Rowden G, Pope B. Tissue distribution of cyclosporine A in the mouse: a clue to toxicity?. Clin Nephrol 25:27-29 (1986).

Birnbaum J, Kahan FM, Kropp H, MacDonald JS, Carbapenems, a new class of betalactam antibiotics. Discovery and development of imipenem/cilastatin. Am J Med 78:3-21 (1985).

Calne RY, White DJ, Thiru S, Evans DB, McMaster P, Dunn DC, Craddock GN, Pentlow BD. Cyclosporin A in patients receiving renal allograft from cadaver donors. Lancet 23:1323-1327 (1978).

Campbell BJ, Di Shih Y, Forrester LJ, Zahler WL. Specificity and inhibition studies of human renal dipeptidase. Biochim Biophys Acta 21;956(2):110-118 (1988).

Campbell BJ, Forrester LJ, Zahler WL, Burks M. Beta-lactamase activity of purified and partially characterized human renal dipeptidase. J Biol Chem 10:259(23):14586-14590 (1984).

Campbell BJ, Lin YC, Davis RV, Ballew E. The purification and properties of a particulate renal dipeptidase. Biochim Biophys Acta 5;118(2):371-386 (1966).

Carmellini M, Frosini F, Filipponi F, Boggi U, Mosca F. Effect of cilastatin on cyclosporine-induced acute nephrotoxicity in kidney transplant recipients. Transplantation 64:164-166 (1997).

Carmellini M, Matteucci E, Boggi U, Cecconi S, Giampietro O, Mosca F Imipenem/cilastatin reduces cyclosporin-induced tubular damage in kidney transplant recipients. Transplant Proc 30(5):2034-2035 (1998).

Clissold SP, Todd PA, Campoli-Richards DM. Imipenem/cilastatin. A review of I ts antibacterial activity, pharmacokinetic properties and therapeutic efficacy. Drugs 33(3): 183-241 (1987).

Drusano GL, Standiford HC, Bustamante CI, Forrest A, Rivera G, Tatem B, Schimpff SC. The plasma pharmacokinetics of high dose (1 g) imipenem coadministered with 1 g cilastatin in six normal volunteers. Eur J Clin Microbiol 3(5):468-70 (1984).

Drusano GL, Standiford HC, Bustamante CI, Rivera G, Forrest A, Leslie J, Tatem B, Delaportas D, Schimpff SC. Safety and tolerability of multiple doses of imipenem/cilastatin. Clin Pharmacol Ther 37(5):539-543(1985).

Garcia del Moral R, O'Valle F, Andujar M, Aguilar M, Lucena MA, Lopez-Hidalgo J, Ramirez C, Medina-Cano MT, Aguilar D, Gomez-Morales M. Relationship between P-glycoprotein expression and cyclosporin A in kidney. An immunohistological and cell culture study. Am J Pathol 146:398-408 (1995).

Greenstein, J. P. Advances in enzymology and related subjects of biochemistry. F. F. Nord (ed) Interscience Publishers, Inc. New York (8): 117-169.

Gruss E, Tomas JF, Bernis C, Rodriguez F, Traver JA, Fernandez-Ranada JM. Nephroprotective effect of cilastatin in allogeneic bone marrow transplantation. Results from a retrospective analysis. Bone Marrow Transplant 18:761-765 (1996).

Gyure, WL. Comparison of several methods for semiquantitative determination of urinary protein. Clin. Chem. 23: 876-879 (1977).

Hammer C, Thies JC, Mraz W, Mihatsch M. Reduction of cyclosporin nephrotoxcity by imipenem/cilastatin after kidney transplantation in rats. Transplant proc 21:931-936(1989).

Handschumacher RE, Harding MW, Rice J, Drugge RJ, Speicher DW. Cyclophilin: a specific cytosolic binding protein for cyclosporin A. Science 226(4674)544-547 (1984).

Hooper NM. Glycosyl-phosphatidyl inositol anchored membrane enzymes. Clin Chim Acta 266(1):3-12(1997).

Jackson NM, O'Connor RP, Humes HD. Cyclosporine effects on isolated membranes, proximal tubule cells, and interstitium of the kidney. Transplant Proc 20:748-758 (1988).

JH Lin, I-W Chen, EH Ulm Dose-dependent kinetics of cilastatin in laboratory animals. Drug Metabolism and Disposition. 1989. 17(4):426-432.

Kahan BD. Cyclosporin. New Engl J Med 321:1725-1728 (1989).

Kahan BD. The First International Congress on cyclosporine. Houston, Tex. May 16-19, 1983. Dial Transplant 16: 620-630 (1983).

Kahan FM, Kropp H, Sundelof JG, Birnbaum J. Thienamycin: development of imipenen-cilastatin. J Antimicrob Chemother 12 Suppl D:1-35 (1983).

Kahan JS, Kahan FM, Goegelman R, Currie SA, Jackson M, Stapley EO, Miller TW, Miller AK, Hendlin D, Mochales S, Hernandez S, Woodruff HB, Birnbaum J. Thienamycin, a new beta-lactam antibiotic. I. Discovery, taxonomy, isolation and physical properties. J Antibiot (Tokyo) 32(1): 1-12(1979).

Kim JY. GW Kim, SH Choi, JS We, HS Park, J Yang: Renal Dehydropeptidase-I(DHPI) stability and pharmacokinetics of DA-1131, a new carbapenem antibiotic 1996, abstr III P-45, p 238. In Abstracts of the Annual Meeting of the Korea Society of Applied Pharmacology, Seoul National University, Seoul, Korea.

Kim SH, JW Kwon, WB Kim, MG Lee: Effects of cilastatin on the pharmacokinetics of a new carbapenem, DA-1131, in rats, rabbits and dogs. Antimicrobial Agents and Chemotherapy, 1999; 43(10):2524-2527.

Klintmalm GB, Iwatsuki S, Starzl TE. Nephrotoxicity of cyclosporin A in liver and kidney transplant patients. Lancet 28:470-1 (1981).

Koller M, Brom J, Raulf M, Konig W. Cilastatin (MK 0791) is a potent and specific inhibitor of the renal leukotriene D4-dipeptidase. Biochem Biophys Res Commun 16:131 (2):974-979 (1985).

Kozak EM, Tate SS. Glutathione-degrading enzymes of microvillus membranes. J Biol Chem 10:257(11):6322-6327 (1982).

Kropp H, Sundelof JG, Hajdu R Kahan FM 1982 M Kusama, K Yamamoto, H Yamada, H Kotaki, H Sato, T Iga: Effect of Cilastatin on renal handling of Vancomycin in Rats. 1998 Journal of Pharmaceutical Sciences: 87 (9): 1173-1176.

Markewitz A, Hammer C, Pfeiffer M, Zahn S, Drechsel J, Reichenspurner H, Reichart B. Reduction of cyclosporine-induced nephrotoxicity by cilastatin following clinical heart transplantation. Transplantation 57:865-870 (1994).

Metabolism of thienamycin and related carbapenems antibiotics by the renal dipeptidase, dehydropeptidase I. Antimicrob Agents Chemother 22:62-70.

Mihatsch MJ, Ryffel B, Hermle M, Brunner FP, Thiel G. Morphology of cyclosporine nephrotoxicity in the rat. Clin Nephrol 25:S2-S8 (1986).

Morandat S, Bortolato M, Roux B. Cholesterol-dependent insertion of glycosylphosphatidylinositol-anchored enzyme. Biochim Biophys Acya. 31;1564(2):473-478 (2002).

Mraz. W, Modic PK, Hammer C. Impact of imipenem/cilastatin on cyclosporine metabolism and excretion. Transplant Proc 24(5):1704-1708 (1992).

Mraz W, Sido B, Knedel M, Hammer C. Concomitant immunosuppressive and antibiotic therapy-reduction of cyclosporine A blood levels due to treatment with imipenem/cilastatin. Transplant Proc 19(5):4017-4020 (1987).

National Institutes of Health Consensus Confererce. JAMA 259:2961 (1983).

Nitanai Y, Satow Y, Adachi H, Tsujimoto M. Crystal structure of human renal dipeptidase involved in beta-lactam hydrolysis. J Mol Biol 321(2):177-84 (2002).

Norbby SR, Alestig K, Bjornegard B, Burman LA, Ferber F, Huber JL, Jones KH, Kahan FM, Kaban JS, Kropp H, Meisinger MA, Sundelof JG. Urinary recovery of N-formimidoyl thienamycin (MK0787) as affected by coadministration of Nforminidoyl thienamycin dehydropeptidase inhibitors. Antimicrob Agents Chemother 23(2):300-307 (1983).

Norrby R, Alestig K, Bjornegard B, Burman L, Ferber F, Kahan F, Huber J, Jones K. 21st ICAAC, (abst n° 592).

Norrby SR 1985 Imipenem/cilastatin: rationale for a fixed combination. Rev. Infect. Dis 7 (Suppl 3): s447-s451.

Nosjean O, Briolay A, Roux B. Mammalian GPI proteins: sorting, membrane residence and functions. Biochim Biophys Acta 8; 1331(2):153-186(1997).

Perez M, Castilla M, Torres AM, Lázaro JA, Sarmiento E, Tejedor A. Nephrol Dial Transplant. 19(10:2445-2455 (2004).

Razani B, Woodman SE, Lisanti MP. Caveolae: from cell biology to animal physiology. Pharmacol Rev 54(3):431-467 (2002).

Ryffel B. Pharmacology of cyclosporine. Cellular activation: regulation of intracellular events by cyclosporine. Pharmacol Rev 41(3):407-422(1990).

Sack K, Herhahn J, Marre R, Schulz E. Renal tolerance of imipenem cilastatin and other beta-lactam antibiotics in rats. Infection 13:S156-60 (1985).

Seveau S, Bierne H, Giroux S, Prevost MC, Cossart P. Role of lipid rafts in E-cadherin—and HGF-R/Met—mediated entry of Listeria monocytogenes into host cells. J Cell Biol 30;166(5):743-753 (2004).

Sido B, Hammer C, Mraz W, Krombach F. Nephroprotective effect of imipenem/cilastatin in reducing cyclosporine toxicity. Transplant proc 1:1755-1758 (1987).

Simons K, Toomre D. Lipid rafts and signal transduction Nat Rev Mol Cell Biol 1(1):31-39 (2000).

Smart EJ, Graf GA, McNiven MA, Sessa WC, Engelman JA, Scherer PE, Okamoto T,Lisanti MP. Caveolins, liquid-ordered domains, and signal transduction. Mol Cell Biol 19(11):7289-7304 (1999).

T Nakamura, Y Hashimoto, T Kokuryo, K-I Inui: Effects of Fosfomycin and Imipenem/Cilastatin on Nephrotoxicity and Renal Excretion of Vancomycin in Rats. Pharmaceutical Research 1998; 15 (5):734-738.

T Toyoguchi Y Nakagawa: Nephrotoxicity and drug interaction of vancomycin (2). Folia Pharmacol Jpn 1996. 107: 225-235.

Tally FP, Jacobus NV, Gorbach SL. In vitro activity of N-formimidoyl thienamycin (MK0787). Antimicrob Agents Chemother 18(4):642-644 (1980).

Tejedor A, Torres AM, Castilla M, Lazaro JA, de Lucas C, Caramelo C. Cilastatin protection against cyclosporin A-induced nephrotoxicity: clinical evidence. Curr Med Res Opin. 2007 March:23(3)505-13.

Thiel G, Mihatsch M, Landmann J, Hermle M, Brunner FP, Harder F. Is cyclosporine A-induced nephrotoxicity in recipients of renal allografts progressive? Transplant Proc 17:169-178 (1985).

Toyoguchi T, Takahashi S, Hosoya J, Nakagawa Y, Watanabe H. Nephrotoxicity of vancomycin and drug interaction study with cilastatin in rabbits. Antimicrob Agents Chemother 41(9):1985-1990 (1997).

Tropschug M, Barthelmess IB, Neupert W. Sensitivity to cyclosporing A is mediated by cyclophilin in Neurospora crassa and *Saccharomyces cerevisiae*. Nature 21-28:953-955 (1989).

Welch CL, Campbell BJ. Uptake of glycine from L-alanyl-glycine into renal brush border vesicles. J Membr Biol 54(1):39-50 (1980).

Yamada E. The fine structure of the gall bladder epithelium of the mouse. J Biophys Biochem Cytol 25;1(5):445-458 (1955).

What is claimed is:

1. A method of decreasing apoptosis of proximal tubule cells containing cholesterol rafts and expressing DHP-I, the method comprising administering cilastatin and a nephrotoxic compound that is not a substrate of DHP-I to a subject in need thereof, wherein:
the proximal tubule cells are in apoptosis caused by the nephrotoxic compound; and
the nephrotoxic compound is selected from the group consisting of gentamicin, cisplatin, an iodinated contrast agent, foscarnet, mannitol, amphotericin B, acetaminophen and chloroform.

2. The method according to claim 1, wherein the nephrotoxic compound is gentamicin.

3. The method according to claim 1, wherein the nephrotoxic compound is foscarnet.

4. The method according to claim 1, wherein the nephrotoxic compound is amphotericin B.

5. The method according to claim 1, wherein the nephrotoxic compound is mannitol.

6. The method according to claim 1, wherein the nephrotoxic compound is cisplatin.

7. The method according to claim 1, wherein the nephrotoxic compound is an iodinated contrast agent.

8. The method according to claim 7, wherein the iodinated contrast agent is iopamidol.

9. The method according to claim 1, wherein the nephrotoxic compound is acetaminophen.

10. The method according to claim 1, wherein the nephrotoxic compound is chloroform.

11. The method according to claim 1, wherein the cilastatin is incorporated into a medicament that is designed to be administered via the oral, intramuscular, peritoneal or intravenous route.

12. The method according to claim 11, wherein the medicament is designed to be administered via the intravenous route.

13. The method according to claim 12, wherein the medicament containing cilastatin is designed to be administered in such a manner that the dose of cilastatin received by the subject is at least 750 mg/day.

14. The method according to claim 13, wherein the medicament containing cilastatin is designed to be administered in such a manner that the daily dose of cilastatin may be administered in a single daily dose.

15. The method according to claim 13, wherein the medicament containing cilastatin is designed to be administered in such manner that the daily dose of cilastatin may be administered in at least two daily doses.

16. The method according to claim 1, wherein the nephrotoxic compound is cationic or neutral at physiological pH.

17. The method according to claim 1, wherein the cilastatin is incorporated into a medicinal product which comprises both cilastatin and the nephrotoxic compound.

18. A therapeutic method to reduce the apoptosis caused by a compound that is not a substrate of DHP-I, the method comprising the administration of cilastatin to a subject receiving the compound, wherein:
the individual has proximal tubule cells in apoptosis caused by the compound; and
the compound is a nephrotoxic compound selected from the group consisting of gentamicin, cisplatin, an iodinated contrast agent, foscarnet, mannitol, amphotericin B, acetaminophen and chloroform.

19. The method according to claim 18, wherein the cilastatin is administered simultaneously with the nephrotoxic compound.

20. The method according to claim 19, wherein the cilastatin is administered by means of additional successive doses subsequent to the administration of the nephrotoxic compound.

21. The method according to claim 20, wherein the cilastatin is administered via an oral, intramuscular, peritoneal or intravenous route.

22. The method according to claim 21, wherein the cilastatin is administered via an intravenous route.

23. The method according to claim 22, wherein the cilastatin is administered dissolved in saline solution.

24. The method according to claim 22, wherein the cilastatin is administered at a daily dose of at least 750 mg/day.

25. The method according to claim 24, wherein the cilastatin is administered in a single daily dose.

26. The method according to claim 24, wherein the cilastatin is administered in at least two daily doses.

27. The method according to claim 18, wherein the subject to be treated is a human being.

* * * * *